United States Patent [19]
Kennedy et al.

[11] Patent Number: 5,505,946
[45] Date of Patent: Apr. 9, 1996

[54] BOWMAN-BIRK INHIBITOR CONCENTRATE COMPOSITIONS AND METHODS FOR THE TREATMENT OF PRE-MALIGNANT TISSUE

[75] Inventors: Ann R. Kennedy, Wynnewood, Pa.; Bernard F. Szuhaj, Fort Wayne, Ind.

[73] Assignees: Trustees of Univ of PA, Philadelphia, Pa.; Central Soya Co, Inc., Ft. Wayne, Ind.

[21] Appl. No.: 221,582

[22] Filed: Apr. 1, 1994

[51] Int. Cl.⁶ .................................................. A61K 35/78
[52] U.S. Cl. .......................................... 424/195.1; 514/783
[58] Field of Search ........................... 424/195.1; 514/283

[56] References Cited

U.S. PATENT DOCUMENTS 4,793,996  12/1988  Kennedy et al. ............... 424/195.1
5,217,717  6/1993  Kennedy et al. ............... 424/195.1

OTHER PUBLICATIONS

Baturay et al., "Pyrene Acts as a Cocarcinogen with the Carcinogens Benzo[A]pyrene, β–Propiolactone and Radiation in the Induction of Malignant Transformation in Cultured Mouse Fibroblasts; Soybean Extract Containing the Bowman–Birk Inhibitor Acts as an Anticarcinogen", *Cell Biology and Toxicology* 1986, 2, 21–32.

Birk et al., "*Bull. Res. Council Israel*" 1962, Sec. 1, 11, 48.

Birk et al., "Separation of a Tribolium–protease inhibitor from soybeans on a calcium phosphate column", *Biochim. Biophys. Acta* 1963, 67, 326.

Bowman, "Differentiation of Soy Bean Antitrypic Factors", *Proc. Soc. Exptl. Med.* 1946, 63, 547.

Hwang et al., "Purification, Partial Characterization and Immunological Relationships of Multiple Low Molecular Weight Protease Inhibitors of Soybean", *Biochim. Biophys. Acta* 1977, 495, 369–382.

Kennedy et al., "Anticarcinogenic Actions of Protease Inhibitors", *Anticarcinogenesis and Radiation Protection*, edited by Cerutti et al., Plenum Pub. Co., pp. 285–295 (1987).

Messadi et al., "Inhibition of Oral Carcinogenesis by a Protease Inhibitor", *JNCI* 1986, 76, 447–452.

Perlmann et al., *Methods in Enzymology Volume XIX*, "Bowman–Birk Inhibitor from Soybeans (Inhibitor AA)", 1970, 19, 860–861.

St. Clair et al., "Suppression of Dimethylhydrazine–induced Carcinogenesis in Mice by Dietary Addition of the Bowman–Birk Protease Inhibitor", *Cancer Res.* 1990, 50, 580–586.

Weed et al., "Protection against dimethylhydrazine–induced adenomatous tumors of the mouse colon by the dietary addition of an extract of soybeans containing the Bowman–Birk protease inhibitor", *Carcinogenesis* 1985, 6, 1239–1241.

Yavelow et al., "Bowman–Birk Soybean Protease Inhibitor as an Anticarcinogen", *Cancer Res.* 1983, 43, 2454–2459.

Yavelow et al., "Nanomolar concentrations of Bowman–Birk soybean protease inhibitor suppress x–ray–induced transformation in vitro", *Proc. Natl. Acad. Sci. USA* 1985, 82, 5395–5399.

*Primary Examiner*—John W. Rollins
*Attorney, Agent, or Firm*—Jane Massey Licata

[57] ABSTRACT

A composition containing a Bowman-Birk Inhibitor Concentrate (BBIC) for the treatment of pre-malignant tissue is provided. Methods of using this composition in the prevention of cancer are also provided.

8 Claims, 7 Drawing Sheets

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 3
( B ) TYPE: amino acid
( D ) TOPOLOGY: linear ( x i ) SEQUENCE DESCRIPTION: SEQ ID NO: 1:

Val   Pro   Arg
1

( 2 ) INFORMATION FOR SEQ ID NO: 2:

( i ) SEQUENCE CHARACTERISTICS:
( A ) LENGTH: 3
( B ) TYPE: amino acid
( D ) TOPOLOGY: linear ( x i ) SEQUENCE DESCRIPTION: SEQ ID NO: 2:

Val   Leu   Lys (2) INFORMATION FOR SEQ ID NO: 3:

(i) SEQUENCE CHARACTERISTICS:
        (A) LENGTH: 3
        (B) TYPE: amino acid
        (D) TOPOLOGY: linear (xi) SEQUENCE DESCRIPTION: SEQ ID NO: 3:

Glx Gly Arg
    1

(2) INFORMATION FOR SEQ ID NO: 4:

(i) SEQUENCE CHARACTERISTICS:
        (A) LENGTH:
        (B) TYPE: amino acid
        (D) TOPOLOGY: linear (xi) SEQUENCE DESCRIPTION: SEQ ID NO: 4:

Gly Pro Leu Gly Pro
                    5

BOWMAN-BIRK INHIBITOR CONCENTRATE COMPOSITIONS AND METHODS FOR THE TREATMENT OF PRE-MALIGNANT TISSUE

BACKGROUND OF THE INVENTION

This invention relates to a composition comprising a Bowman-Birk Inhibitor Concentrate (BBIC) product prepared from the soybean and uses thereof. This BBIC product has been shown to exhibit surprisingly high inhibitory activity against the malignant transformation of cells under certain conditions and its administration to affect various forms of cancer development. It is now believed that BBIC inhibits the malignant transformation of cells by destroying pre-malignant tissue by the induction of high levels of proteolytic activity.

It has been shown that the enzyme-inhibitor described by Bowman, *Proc. Soc. Exptl. Med.* 1946, 63, 547 and Birk et al., *Bull. Res. Council Israel* 1962, Sec. 1, 11, 48 and *Biochim. Biophys. Acta* 1963, 67, 326, and subsequently referred to as the Bowman-Birk Inhibitor (BBI), possesses certain physiological activity that prevents, or at least greatly reduces, radiologically or chemically induced malignant transformation of cells in culture and in experimental animals.

Yavelow et al., *Proc. Natl. Acad. Sci. USA* 1985, 82, 5395–5399, reported that a crude soybean extract, if defatted with acetone, effectively blocked cell transformation in vitro. These observations, with epidemiological data, suggested BBI as a putative dietary anticarcinogen, particularly with respect to colon cancer.

Weed et al., *Carcinogenesis* 1985, 6, 1239–1241, disclose that an extract of soybeans containing the Bowman-Birk protease inhibitor added to the diet of dimethylhydrazine (DMH)-treated mice resulted in a significant suppression of adenomatous tumors of the colonic mucosa. DMH-induced colon cancer in mice is generally regarded as an excellent animal model for the human disease, with carcinogen treatment inducing adenocarcinomas of the colon and rectum which are similar to the tumors arising in the human colon suggesting the possibility that a dietary additive of the sort studied might confer some protection against the development of human colon cancer without undesirable side effects. The BBI extract and methods for its preparation were as described by Yavelow et al., *Cancer Res.* 1983, 43, 2454–2459; *Proc. Natl. Acad. Sci. USA* 1985, 82, 5395–5399 and Hwang et al., *Biochim. Biophys. Acta* 1977, 495, 369–382.

Messadi et al., *JNCI* 1986, 76, 447–452 demonstrated that a soybean extract containing the protease inhibitor BBI suppresses 7, 12-dimethyl-benz[a]anthracene (DMBA)-induced carcinogenesis in the hamster cheek pouch. This oral cancer model has the same histopathology, growth pattern and precancerous lesions as the most common form of human oral cancer, squamous cell carcinoma. It was shown in this study that hamster cheek pouch carcinogenesis can be inhibited by BBI and suggested that human oral carcinogenesis might respond to BBI in a comparable manner. The BBI preparation used in this study was a crude extract of the inhibitor prepared as described by Yavelow et al., *Proc. Natl. Acad. Sci. USA* 1985, 82, 5395–5399.

Baturay et al., *Cell Biology and Toxicology* 1986, 2, 21–32 disclose that a BBI preparation, wherein a crude soybean extract is defatted with acetone, suppresses radiation and chemically induced transformation in vitro, with or without enhancement by the co-carcinogen, pyrene. Yavelow et al., 1985, show that either pure BBI or the BBI extract prepared in accordance with their methods suppresses radiation induced transformation in C3H10T1/2 cells. Kennedy et al., 1984, report that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast and liver carcinogenesis in vivo.

Kennedy et al. in *Anticarcinogenesis and Radiation Protection*, edited by Cerutti et al., Plenum Pub. Co., pp. 285–295 (1987), disclose that BBI suppresses carcinogenesis in various systems using a crude BBI extract prepared by defatting soybeans with acetone. Their results suggested that very low concentrations of BBI-type protease inhibitor preparations would be effective as chemopreventive agents for colon cancer. There was no evidence to suggest that the use of protease inhibitors as chemopreventive agents would be complicated by possible toxicity problems.

St. Clair et al., *Cancer Res.* 1990, 50, 580–586, report that the addition of 0.5% or 0.1% semi-purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less had no adverse effect upon the health of the mice but had the capacity to suppress liver and colon carcinogenesis.

Perlmann et al., *Methods in Enzymology* 1970, 19, 860–861, have described an elaborate method for obtaining BBI from a defatted soybean extract.

U.S. Pat. No. 4,793,996 (Kennedy et al.) discloses a process comprising treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step taught by Perlmann et al.

Kennedy et al. teach that it is unnecessary to carry out a procedure requiring complete purification of the extract to the point where the product contains only a single protein. Instead, they found it effective to stop the purification procedure at a point where a crude inhibitor extract is obtained. This crude extract is itself edible and can be used as an inhibitor of malignant transformation of cells, for example, by oral ingestion. Kennedy et al. disclose a process for preparing a crude soybean extract containing an inhibitor of malignant cell transformation which comprises defatting soybeans and extracting said inhibitor from said defatted soybeans. The improvement comprises defatting said soybeans by bringing them into contact with at least an equal weight of acetone and, thus, producing a crude inhibitor extract having greatly increased effectiveness.

The prior art has also described concentration of BBI from soybean solubles by centrifugation and ultrafiltration, and further purification by acetone precipitation. The separation of soybean solids from hexane-extracted soy flour/flakes in a commercial soy protein concentrate process is well known. However, the BBIC product of this invention produced by these steps alone, i.e., without the use of an aqueous alcohol extraction, is both novel and unexpected as this BBIC product is unexpectedly more effective in suppressing cancer development.

Furthermore, production of this BBIC product uses less solvent and thus is a more economical and safer process. Producing waste-solvent streams containing a mixture of alcohol-water-acetone requires very complex and expensive distillation equipment, which is eliminated in the present invention. It has also been discovered that ultrafiltration is much more efficient than dialysis; one single step of ultrafiltration can remove more solids than three days of dialysis. After purification, most of the examples of the present invention employ spray-drying, which is much faster and hence, more economical than the lyophilization described in the prior art. Unexpectedly, spray-drying has no effect on BBI recovery, as measured by Chymotrypsin Inhibitor (CI) content, used as an indicator for the presence of BBI.

SUMMARY OF THE INVENTION

In the present invention, an effective Bowman-Birk Inhibitor Concentrate product is provided having a high level of biological activity as measured by chymotrypsin inhibitory (CI) content and/or the inhibition of the malignant transformation of cells. A method which produces compositions of the present invention utilizes soybean solubles as a source material that can be recovered directly from a commercial acid-leached soy protein concentrate process. The soybean solubles are diluted with water to 15–25% solids content, followed by centrifugation to produce purified soybean solubles. The purified solubles are then diluted to 10–12% solids with water to produce reslurried purified soybean solubles. The reslurried solubles are then subjected to ultrafiltration to produce a "crude" BBI concentrate (CBBIC). The CBBIC is then diluted with water and spray-dried to produce a BBI concentrate (BBIC) product. In other embodiments of the invention, the diluted CBBIC is subjected to another ultrafiltration step to produce a "semi-crude" BBI concentrate (SCBBIC) which is then spray-dried to produce a BBI concentrate (BBIC) product. In a preferred embodiment, the SCBBIC is treated with acetone to produce a BBI concentrate precipitate. After settling and decanting, the resulting purified BBI concentrate precipitate is air-dried, ground, reslurried with water, filtered and then lyophilized or spray-dried to produce a BBI concentrate (BBIC) product. In another embodiment, the time-consuming ultrafiltration step(s) are eliminated by starting with soy solubles and applying the acetone treatment to a substrate that has a substantially higher concentration of BBI than that in the defatted soy flour/flake of the prior art, resulting in a more economical means of producing the BBIC product of the invention.

It was surprisingly found that the BBIC product of the present invention, produced in accordance with any of the described methods, is a significantly improved inhibitor of malignant cell transformation over prior art BBI products. Methods for the administration of said BBIC product to inhibit the malignant transformation of cells and to prevent or inhibit the progression of cancer are also provided.

DETAILED DESCRIPTION OF THE INVENTION

Figure 1:
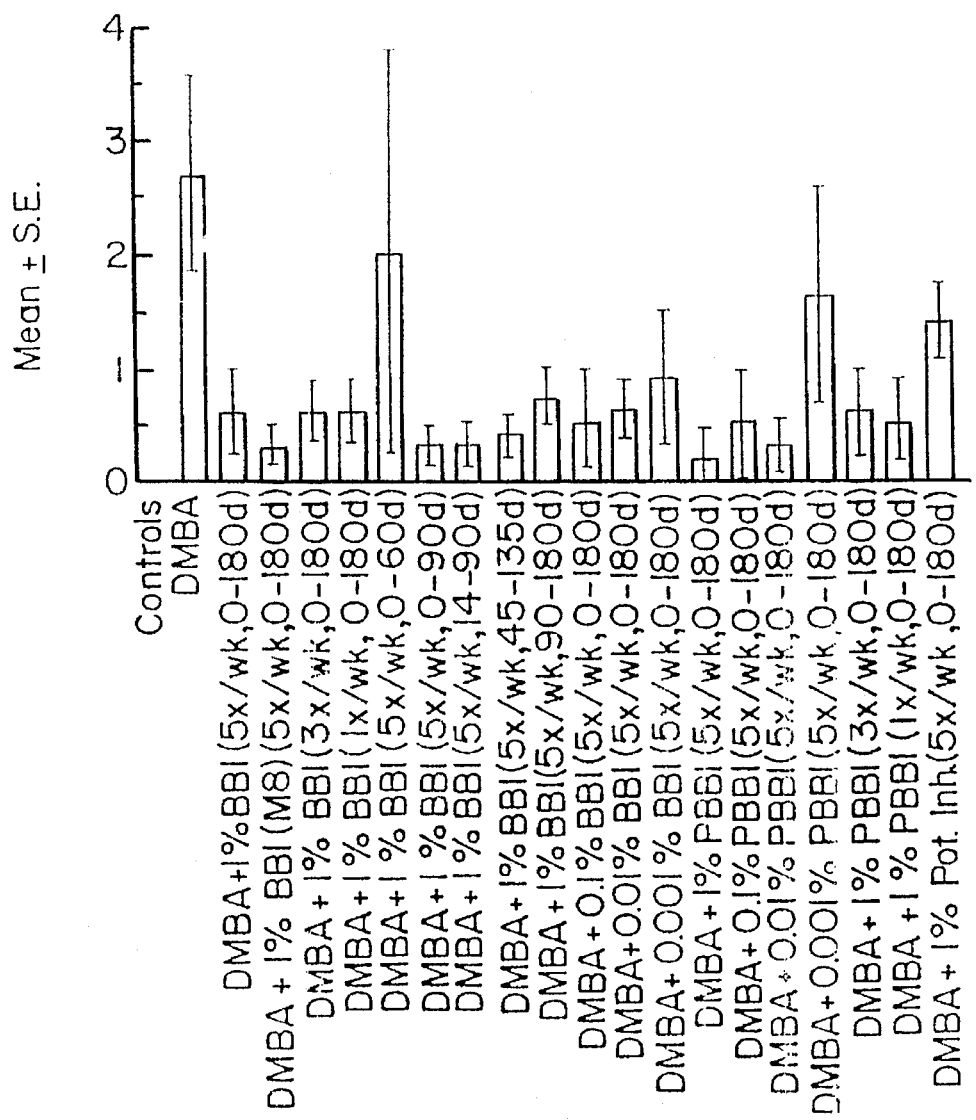
FIG. 1 is a histogram showing the number of tumors observed in the animal study treatment groups.

In the present invention compositions for the treatment of pre-malignant tissues are provided which comprise a BBI concentrate (BBIC) product. In a preferred embodiment, these compositions further comprise a pharmaceutically acceptable carrier. These compositions are useful in the treatment of pre-malignant tissues wherein an effective amount of a composition comprising a BBIC product is administered to animals bearing pre-malignant lesions. The compositions are especially useful in the prevention of cancers and in the treatment of pre-malignant lesions of organs or tissues including, but not limited to, esophagus, liver, lung, breast, colon, oral mucosa, hematopoietic and prostate. In accordance with the present invention, soybean solubles, preferably produced from acidic, aqueous-extracted, hexane-defatted soybeans, are diluted in an aqueous solution, preferably water, to form a slurry. Preferably the slurry contains about 10–25% solids. The aqueous soluble portion of the soybean solubles is separated from the slurry, preferably by centrifugation, to produce a purified soybean soluble composition. This composition is diluted in an aqueous solution, preferably water, to produce reslurried purified soybean solubles. This slurry is then ultrafiltered, preferably with a 1,000 MW membrane, to form a crude Bowman-Birk Inhibitor Concentrate (CBBIC). This ultrafiltration step can be repeated to produce a "semi-crude" BBI concentrate (SCBBIC).

In one embodiment, the crude or semi-crude concentrate is treated with acetone to produce a BBI concentrate precipitate. After settling and decanting, the resulting BBI concentrate precipitate is dried, reslurried in aqueous solution, filtered and then lyophilized to produce a BBI concentrate (BBIC) product.

In another embodiment of the invention, purified soybean solubles are produced as described above and then diluted to about 10% solids. The resulting reslurried purified soybean solubles are then treated as described above to produce a SCBBIC which is treated with acetone to produce a BBI concentrate precipitate. A BBI concentrate (BBIC) product is produced from this precipitate as described above, with the exception that the filtered precipitate is spray dried rather than lyophilized.

In another embodiment of the invention, soybean solubles are diluted with an aqueous solution, preferably water, and separated by centrifugation to produce purified soybean solubles. The purified solubles are diluted in an aqueous solution, preferably water, to produce reslurried purified soybean solubles which are subjected to ultrafiltration, preferably with a 1,000 MW membrane. The resulting CBBIC is diluted with water (1:1) and spray dried to produce a BBI concentrate (BBIC) product.

In another embodiment of the invention, the CBBIC is diluted with water and again subjected to ultrafiltration, preferably with a 1,000 MW membrane, to produce a SCBBIC which is spray dried to produce a BBI concentrate (BBIC) product.

In yet another embodiment of the invention, the ultrafiltration step(s) are eliminated by starting with soy solubles and applying the acetone treatment to a substrate that has a substantially higher concentration of BBI than that in acidic, aqueous-extracted, hexane-defatted soybeans. Soybean solubles are centrifuged to produce purified soybean solubles. Acetone is added to the supernatant to produce a CBBIC precipitate which is allowed to settle. The resulting precipitate containing the partially purified BBI is then resuspended in water and centrifuged. Acetone is added to the supernatant and the resulting water soluble, acetone insoluble precipitate allowed to settle. The precipitate is then dried to produce a BBI concentrate (BBIC) product.

The BBI concentrate (BBIC) product produced can then be used in a composition, either alone or in combination with a pharmaceutically acceptable carrier, for the prevention of cancer or the treatment of pre-malignant lesions. Data from experiments with the claimed compositions have indicated that such compositions may be especially effective in the prevention of cancer in the following organs or tissues: colon, oral mucosa, esophagus, liver, lung and hematopoietic. From preliminary data, it is expected that BBIC will also prevent cancers of the breast and prostate and will be able to eradicate pre-malignant lesions in these organs.

It has been observed that the claimed compositions comprising a BBIC product are highly effective at suppressing DMBA-induced oral carcinogenesis in hamsters at concentrations as low as 0.01%. In studies performed comparing the compositions of the present invention with those of the prior art, the BBIC composition of the present invention was found to be more effective in the suppression of oral carcinogenesis in hamsters than BBI product prepared by methods described in the prior art. It has also been discovered that in in vitro experiments BBIC compositions are effective at concentrations an order of magnitude lower than BBI compositions of the prior art.

The BBIC compositions of the present invention are useful for inhibiting the malignant transformation of cells. Administering these compositions, either alone or in combination with a pharmaceutically acceptable carrier, is useful for preventing cancer or inhibiting cancer progression in an animal, such as man. The BBIC compositions are believed to be especially effective against breast, colon and prostate cancer as these forms of cancer are known to be greatly reduced in populations consuming high levels of soybean products in their diets. Administration of an effective amount of the claimed compositions, either as a prophylactic dietary supplement or a pharmaceutical, is within the teachings of the invention. The term "effective amount" refers to an amount which prevents cells from becoming cancerous or, in the case of hematopoietic tissue, deters the growth of cancerous cells. Such an amount can be determined by those of skill in the art in accordance with known methods. Compositions of the present invention may be administered parenterally, rectally, topically, transdermally or orally, preferably orally. Examples of pharmaceutical or prophylactic dietary supplement formulations include, but are not limited to, syrups, suspensions, emulsions, tablets, capsules and lozenges.

One embodiment of the invention is a liquid formulation comprising a suspension or solution of the composition in a pharmaceutically acceptable liquid carrier. Suitable liquid carriers include, but are not limited to, ethanol, glycerin, non-aqueous solvents such as polyethylene glycols, oils or water with a suspending agent, preservatives, flavorings or coloring agents, or any suitable combination thereof.

In another embodiment, a composition in the form of a tablet is prepared using any suitable pharmaceutical carrier routinely used for preparing solid formulations. Examples of such carriers include, but are not limited to, magnesium stearate, starch, lactose, sucrose and cellulose.

Compositions in the form of capsules are prepared using routine encapsulating procedure. For example, pellets, granules or powder containing a composition of the instant invention can be prepared using standard carriers and then filled into a hard gelatin capsule. Alternatively, a dispersion or suspension can be prepared using any suitable pharmaceutical carrier(s) and the dispersion or suspension is then filled into a soft gelatin capsule. Suitable pharmaceutical carriers include, but are not limited to, aqueous gums, cellulose, silicates and oils.

In yet another embodiment, a composition for parenteral administration is formulated as a solution or suspension. This solution or suspension will generally include the composition of the instant invention in a sterile aqueous carrier or parenterally acceptable oil. Examples of parenterally acceptable oils include, but are not limited to, polyethylene glycol, polyvinyl pyrrolidone, lecithin, arachis oils and sesame oil. Alternatively, the solution can be lyophilized and then reconstituted with a suitable solvent just prior to administration.

In addition a BBIC composition of the present invention is designed to be a stable mouthwash solution that provides extended mucosal contact time, is palatable, easy to administer and suitable for low cost mass production. A saliva substitute provides the solution with the necessary viscosity to increase mucosal contact time and bioavailability, and has been shown to provide sustained release of many compounds. In one formulation, BBI Concentrate (BBIC) product, a saliva substitute such as sorbitol, carboxymethylcellulose, or methylparaben and water are included.

Single dose (steady state) pharmacokinetic studies of BBIC compositions have been performed. Long term (including some life-span length) studies of BBIC compositions in rats, mice and hamsters have revealed no toxic effects at anticarcinogenic levels in the diet; the levels of BBIC studied in animals are well over an order of magnitude higher than the highest dose proposed for human use (when the amounts administered to animals on a weight basis are extrapolated to man) and are, therefore, believed to be safe.

The BBIC compositions of the present invention are currently being studied in treatment of pre-malignant lesions of the oral mucosa. "Oral mucosa" refers to areas of both the oral and oropharyngeal mucosa including the tongue and lips. Current modalities in the treatment of oral and pharyngeal malignancies have had little to no effect upon overall survival; thus, there is a need for a safe and efficacious chemopreventive agent such as BBIC.

The development of cancer occurs through several steps involving initiation, promotion and progression to malignancy. Premalignant lesions are the first clinically identifiable lesions to occur prior to the development of invasive disease.

In oral cancer, pre-malignant lesions are classified into leukoplakia (a whitish lesion that does not rub off), erythroplakia (a red, inflamed appearing patch of mucosa) or a combination of the two. The risk of developing a carcinoma from these pre-malignant lesions is dependent upon their degree of cell and tissue dysplasia with erythroplakia being a far more ominous predictor of cancer than leukoplakia.

Human trials with BBIC compositions have recently begun. In one study, the effects of BBIC compositions in patients with leukoplakia have been evaluated. In preparation for human trials with BBIC compositions, data were collected on the intermediate marker endpoints (IME) that will be utilized in large scale studies. Findings on levels of proteolytic activity as the IME in human trials are summarized below. For each organ studied in both animal model systems and human samples, levels of certain types of proteolytic activities were determined by substrate hydrolysis. The particular substrates used for these studies are known to be cleaved by proteases whose activity is affected by BBI. Studies on IME in human and animal studies for each organ system studied are described below.

Oral Mucosa

Figure 3:
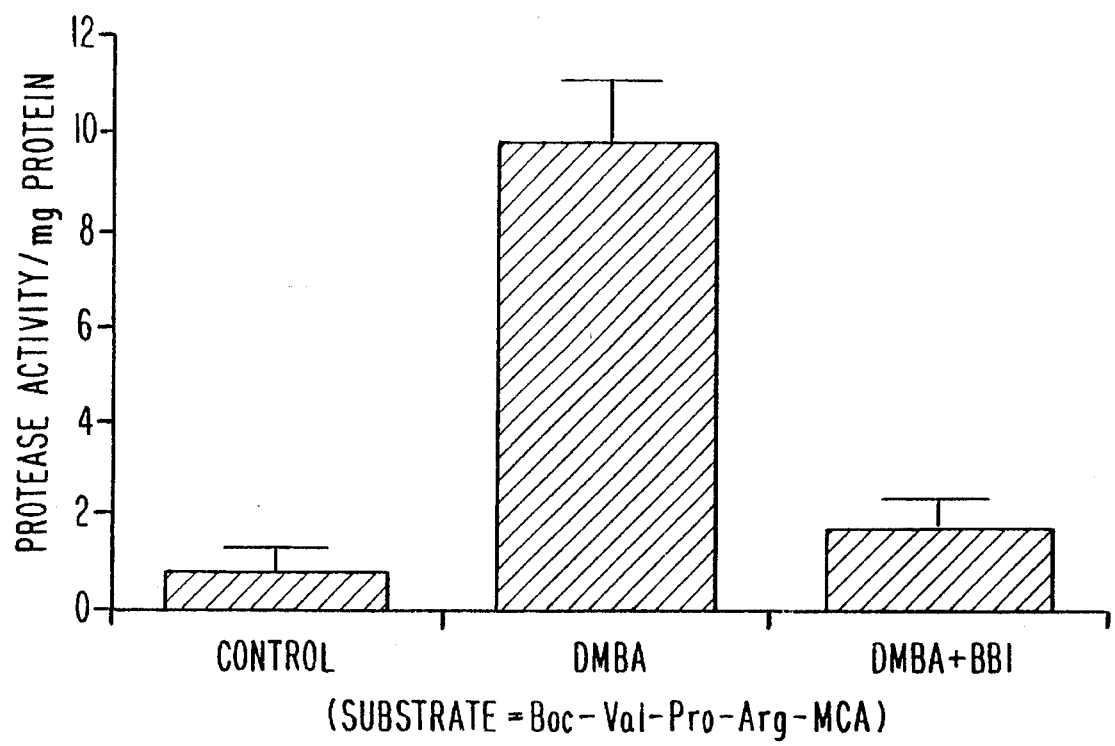
FIG. 3 is a graph showing proteolytic activity in oral buccal mucosa cells of hamsters treated with DMBA with and without BBI. (Substrate 2, SEQ ID NO: 1).

Studies in the oral mucosa in hamsters were begun approximately a decade ago with BBI. However, at that point only the Boc-Val-Pro-Arg-MCA hydrolyzing activity was measured. It was clear from these studies that DMBA treatment of hamster cheek pouches resulted in high levels of Boc-Val-Pro-Arg-MCA hydrolyzing activity in the normal appearing areas of hamster cheek pouch epithelial cells. This activity persisted for long periods of time after carcinogen treatment. In fact, levels of proteolytic activity remained high until the end of the carcinogenesis assay period (months after carcinogen [DMBA] exposure). Proteolytic activities at the end of the carcinogenesis assay period in these studies are shown in FIG. 3. DMBA treatment led to a 10-fold increase in protease levels over normal in normal-appearing areas of DMBA-treated hamster cheek pouch epithelium, while DMBA treatment with BBI exposure resulted in normal levels of activity. This inhibition of proteolytic activity by BBI was correlated with a highly significant suppression of oral carcinogenesis in this system.

Figure 4:
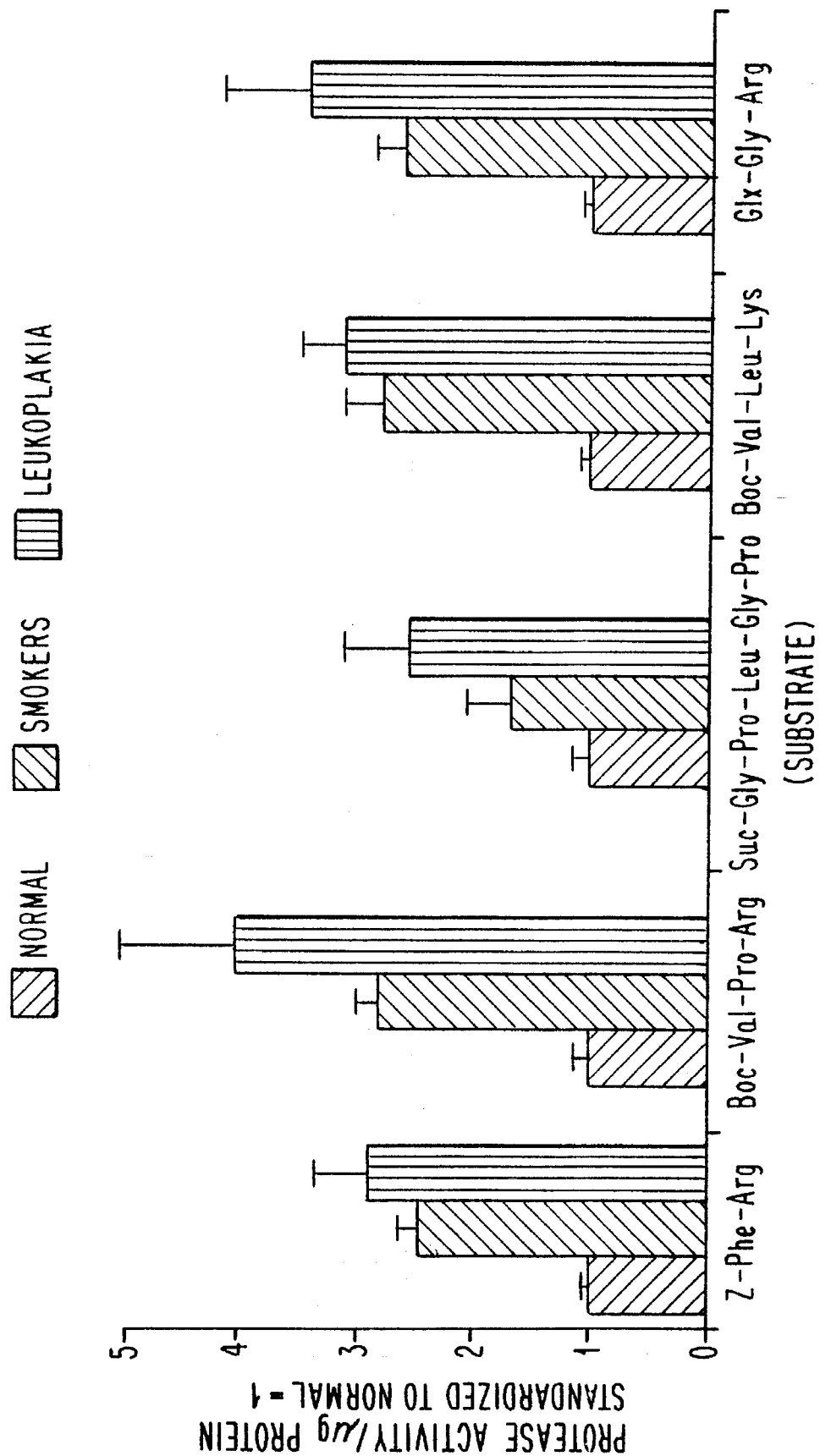
FIG. 4 is a graph showing proteolytic activities in buccal cell samples taken from normal individuals, patients with leukoplakia, and smokers. Substrates corresponding to SEQ ID NOs: 1, 2, 3 and 4 and substrate Z-Phe-Arg were tested.

Studies on the IME in the human oral buccal mucosa have extended to the human trial stage. An extensive amount of data in that tissue has now been collected to characterize the IME in tissue at a higher than normal risk of developing cancer (patients with leukoplakia or erythroplakia) as well as in tissue of normal individuals. Studies in normal individuals have shown some variation in protease levels, with smokers having particularly high levels of the proteolytic activities being studied in human oral buccal mucosa cells. These IME data in people are shown in FIG. 4. The differences observed between normal subjects versus smoking subjects and normal subjects versus patients with leukoplakia or erythroplakia were all significant (for all substrates tested) when tested by a t-test analysis.

Colon mucosal biopsy samples

In these studies, isolated epithelial cell populations from the colons of animals and people gave essentially the same IME results as those obtained with mucosal biopsy specimens. Thus, colon mucosal biopsy specimens were used for the collection of IME data. The major proteolytic activities being studied in the colon carcinogenesis assay systems are being detected by three different substrates, which are: substrate 2—Boc-Val-Pro-Arg (SEQ ID NO: 1); substrate 3—Boc-Val-Leu-Lys (SEQ ID NO: 2); and substrate 4—Glx-Gly-Arg (SEQ ID NO: 3).

Figure 5:
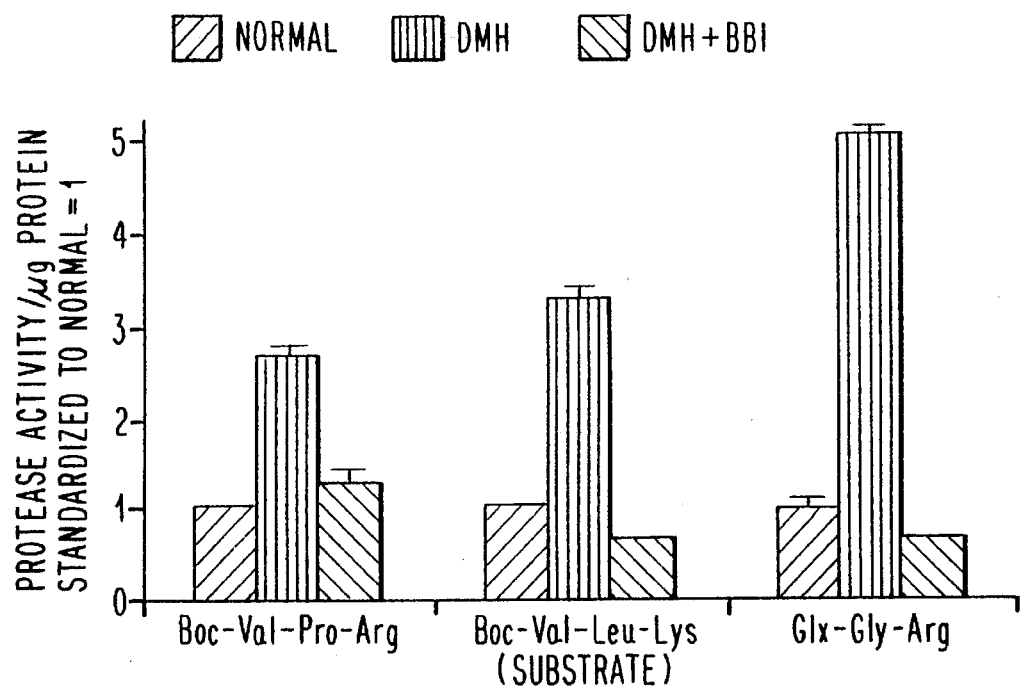
FIG. 5 is a graph showing proteolytic activities in colon mucosal biopsy sections of rats treated with DMH with and without BBI in their diets. Substrates corresponding to SEQ ID NOs: 1, 2 and 3 were tested.

In studies utilizing rats, the animals were untreated or treated with several doses (twice-weekly for three weeks) of dimethylhydrazine (DMH) (known to be at a carcinogenic level; the total DMH dose being 80 mg/kg), with or without 0.1% dietary BBIC. Animals were sacrificed 1 month after the end of the DMH injection period. Protease activity was measured in colonic cells (colon mucosal biopsy samples). Results are shown in histogram form in FIG. 5. It was observed in these studies that one month after DMH treatments, there are highly significant elevations in proteolytic activities, and the activities are at approximately normal levels in DMH-treated animals exposed to BBIC.

As part of the DMH/colon carcinogenesis studies, an experiment was performed to determine the short-term effects of both DMH and BBIC on the IME. This experiment was performed as described:

Nine animals were treated as follows: 3 animals were controls (untreated), 3 animals were treated with a single dose of DMH (13.3 mg/kg), and 3 animals were treated with a single dose of DMH while dietary BBIC was being administered. All animals were sacrificed 48 hours after the single dose of DMH was given. Protease activity was measured in colon cells (colon mucosal biopsy samples) as shown in Table 1:

TABLE 1

Protease Levels in Colon Cells
substrate 2 - Boc—Val—Pro—Arg
substrate 3 - Boc—Val—Leu—Lys
substrate 4 - Glx—Gly—Arg

| Substrate | Control (No treatment) | Protease Activity (Mean ± Std. Dev.) DMH | (RFU/hr/mg protein) DMH + BBIC |
|---|---|---|---|
| Substrate 2 | 7.3 ± 2.3 | 8.5 ± 1.9 | 3.7 ± 0.5 |
| Substrate 3 | 2.4 ± 0.5 | 3.0 ± 0.4 | 1.6 ± 0.2 |
| Substrate 4 | 0.9 ± 0.3 | 1.1 ± 0.3 | 0.6 ± 0.3 |

Protease activity is expressed as relative fluorescent units (RFU)/hr/mg protein. Protease activity was determined as follows. Reactions were carried out in 0.1M Tris (pH 7.5) with the indicated substrate (10 µM) for 1 hour at 37° C. Protease activity was assayed by determining the release of methylamino coumarin (MCA) in a Perkin Elmer LS-5 spectrofluorometer at excitation/emission wavelengths of 380/460 nm, respectively. The spectrofluorometer was standardized such that $10^{-7}$M MCA=700 relative fluorescent units (RFU). The numbers provided in the table are the mean ± standard deviation as determined from several samples taken from 3 different animals from each of the different treatment groups.

The results of the studies in animals show that at a dose of DMH known to be carcinogenic (i.e., known to result in colon cancer development in 50% of the exposed rodents), animals have significantly elevated levels of proteolytic activity 1 month after the last dose of DMH was administered. Under these conditions in which DMH treatments lead to colon cancer in the animals, 0.1% dietary BBIC leads to a highly significant reduction in the number of animals with colon cancer and/or the number of tumors/animal. This dose of dietary BBIC can completely prevent colon carcinogenesis when the dose of DMH is such that 50% or fewer of the animals are destined to get colon cancer and can reduce the number of animals getting colon cancer by approximately 50% when the dose of DMH is such that 70–100% of the animals are destined to get colon cancer. It can be observed in the data shown above that, under conditions in which dietary BBIC reduces the number of animals with colon cancer, BBIC also results in decreased protease levels in the normal appearing areas of colonic epithelium in DMH-treated animals. BBIC treatment is capable of significantly reducing the DMH-elevated protease levels, approximately to the levels observed in untreated control animals. The dose of dietary BBIC used in these animal experiments is comparable to a 200 C.I. unit dose in people (i.e., one of the doses being utilized in human trials with BBIC). The results of the experiment described above show that protease levels in the DMH+BBIC treatment group are significantly reduced when compared to the levels observed in the DMH treatment group as measured by all three of the substrates being utilized in the colon studies. The results for DMH-treated rodents are comparable to those observed for DMBA-treated hamsters in the studies on the inhibition of oral carcinogenesis by BBIC.

Human colon data

Levels of proteolytic activities in colonic cells were determined in colon mucosal biopsies taken from normal subjects or patients with a history of having had one or more adenomatous colon polyps endoscopically resected (HP) or colon cancer (CC). The colon biopsy material was screened with several different substrates; the proteolytic activities known to cleave these substrates have been shown in previous work to be affected by BBI. Data from those substrates exhibiting higher levels of activity in HP or CC patients compared to normal healthy subjects are shown in histogram form in FIG. 6. For these data, levels of proteolytic activities are determined as described above for the relevant animal data. Statistically significant differences in levels of proteolytic activities as detected by all three substrates (p values were generated by a t-test, adjusted when needed to account for unequal variances using Welsh's correction) in normal subjects versus HP patients, patients with ulcerative colitis or patients with colon cancer were observed (i.e., for the data shown in FIG. 6.)

Preliminary human breast data.

Figure 7:
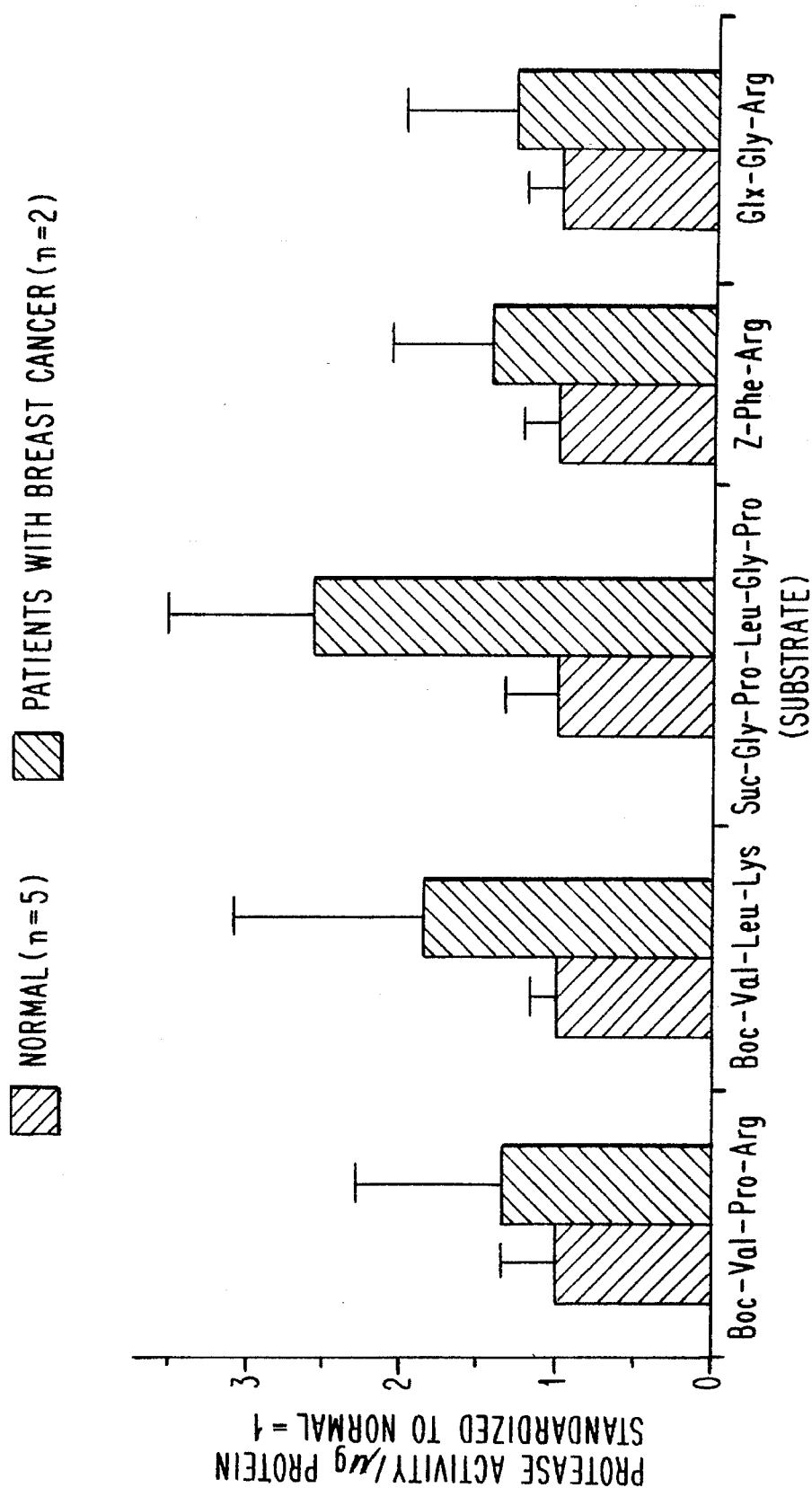
FIG. 7 is a graph showing proteolytic activity in human breast tissue samples in patients with breast cancer or normal individuals; the tissue samples were taken from normal appearing areas of breast tissue in all patients. Substrates corresponding to SEQ ID NOs: 1, 2, 3 and 4 and substrate Z-Phe-Arg were tested.

Samples of human breast tissue have been collected from patients undergoing either benign breast biopsy or mastectomy (i.e., breast surgery for breast cancer). Results from these studies are shown in FIG. 7. As can be observed in FIG. 7, proteolytic activities are elevated with all 5 of the substrates assayed, with protease levels as measured by 3 of the substrates significantly elevated in breast tissue samples taken from patients with breast cancer compared to breast tissue samples removed during benign breast biopsy.

Effects of cancer chemopreventive agents on IME (levels of proteolytic activities as measured by substrate hydrolysis)

As described above, elevated levels of certain types of proteolytic activities known to be affected by BBI are present in cells of pre-malignant tissue (oral leukoplakia or erythroplakia, or Barrett's esophagus), as well as in cells of tissue at a higher than normal risk of cancer development (in colonic epithelium in patients with ulcerative colitis or a previous history of having had one or more colon polyps endoscopically resected or colon cancer or in breast cells taken from normal appearing areas of breast tissue in patients with breast cancer), have been observed.

Results in all of the organs studied showed that there were significantly elevated levels of proteolytic activities in each tissue having a higher than normal risk of cancer development. Thus, levels of proteolytic activity have been used as the IME.

In animals, it has been found that BBIC and other cancer preventive agents reduce the elevated levels of proteolytic activity resulting in normal levels of proteolytic activity. It has also been found that the reduction in the elevated levels of proteolytic activity to normal levels is accompanied by a reversion of the initiated state of the cells such that the cells then have a normal risk of cancer development.

Figure 6:
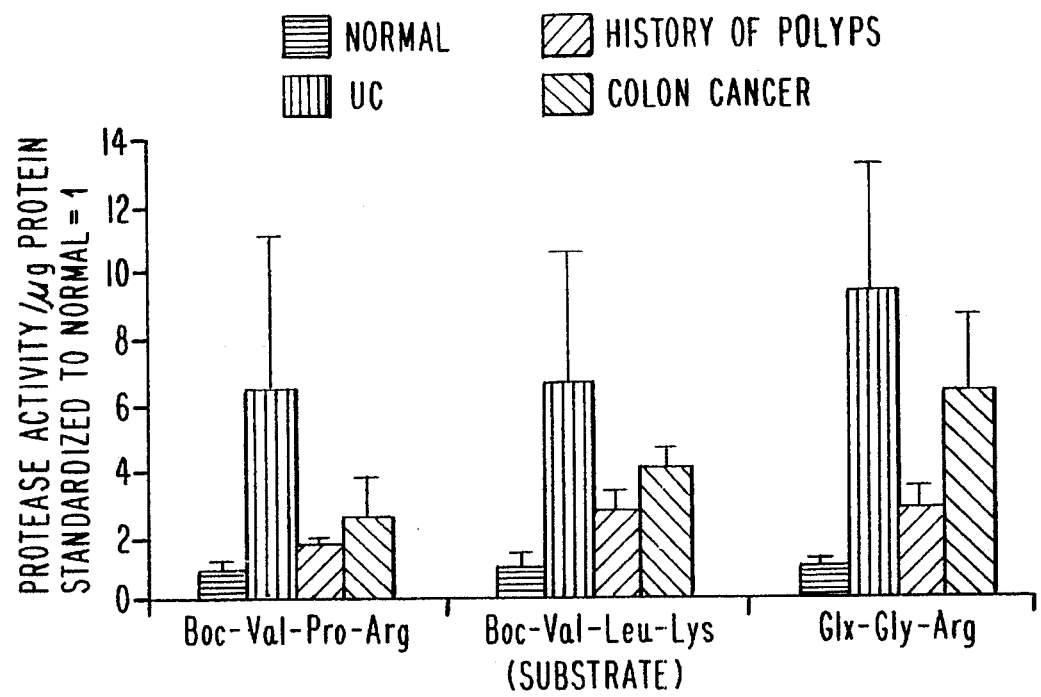
FIG. 6 is a graph showing proteolytic activity in colon mucosal biopsy samples in people at higher than normal risk of developing colon cancer, i.e., those with 1) ulcerative colitis (UC); 2) a history of having had one or more adenomatous polyps endoscopically resected (history of polyps) or 3) patients with colon cancer. Substrates corresponding to SEQ ID NOs: 1, 2 and 3 were tested.

In human tissue, it was observed that tissues having elevated levels of proteolytic activity have a higher than normal risk of developing cancer (See FIGS. 4, 6 and 7). Results for baseline levels of proteolytic activity and measurements at 6 or 24 hours after BBIC treatment in humans are shown in Table 2. In patients with leukoplakia, BBIC treatment unexpectedly resulted in an increase in proteolytic activity in oral buccal mucosa cell as measured by primary substrates used as markers in these studies.

TABLE 2

Protease Levels In Buccal Mucosa Cells Of Patients With Leukoplakia Or Erythroplakia Protease levels were measured at baseline and at 6 hours or 24 hours after treatment with BBIC (25 C. I. units BBIC). Protease levels were measured with the following substrates:
Substrate 1 = Z—Phe—Arg—MCA
Substrate 2 = Boc—Val—Pro—Arg—MCA
Substrate 3 = Boc—Val—Leu—Lys—MCA
Substrate 4 = Glx—Gly—Arg—MCA

| | Patient No. 1 | |
| --- | --- | --- |
| Substrate | Baseline | 6 hour Post-BBI |
| 1 | 41.33 | 61.48 |
| 2 | 64.23 | 96.90 |
| 3 | 33.09 | 41.06 |
| 4 | 105.63 | 153.86 |

| | Patient No. 2 | |
| --- | --- | --- |
| Substrate | Baseline | 24 hour Post-BBI |
| 1 | 176.47 | 307.83 |
| 2 | 514.27 | 1075.00 |
| 3 | 103.33 | 120.17 |
| 4 | 529.27 | 869.67 |

| | Patient No. 3 | |
| --- | --- | --- |
| Substrate | Baseline | 6 hours Post-BBI |
| 1 | 28.52 | 38.34 |
| 2 | 34.64 | 50.22 |
| 3 | 19.69 | 23.52 |
| 4 | 49.13 | 66.15 |

Treatment with another chemopreventive agent, β-carotene, was also found to result in a rise in levels of proteolytic activity in the oral buccal mucosa cells of patients with leukoplakia/erythroplakia, as shown in Table 3. Levels of proteolytic activity in the cells of patients with leukoplakia were compared to mean levels of proteolytic activity observed in all patients diagnosed with oral leukoplakia or erythroplakia.

TABLE 3

Protease Levels in Patients with Leukoplakia/Erythroplakia Who Were Treated with β-carotene Compared to Overall Levels of Activities in Patients with Leukoplakia Protease levels were measured with the following substrates:
Substrate 1 = Z—Phe—Arg—MCA
Substrate 2 = Boc—Val—Pro—Arg—MCA
Substrate 3 = Boc—Val—Leu—Lys—MCA
Substrate 4 = Glx—Gly—Arg—MCA Leukoplakia/Erythroplakia Patients: average of values for 19 patients with Leukoplakia/Erythroplakia

| Substrate | Mean | Standard Deviation |
|---|---|---|
| 1 | 102.43 | 59.81 |
| 2 | 179.16 | 161.15 |
| 3 | 54.61 | 28.28 |
| 4 | 171.41 | 124.85 |

Patient No. 1–3 Months β-carotene Treatment

| | | |
|---|---|---|
| 1 | 223.75 | |
| 2 | 979.25 | |
| 3 | 129.50 | |
| 4 | 542.00 | |

Patient No. 2–3 months β-carotene Treatment

| 1 | 183.85 |
|---|---|
| 2 | 448.85 |
| 3 | 81.35 |
| 4 | 205.81 |

Patient No. 3–6 months β-carotene Treatment

| 1 | 297.76 |
|---|---|
| 2 | 650.00 |
| 3 | 179.76 |
| 4 | 782.12 |

Patient No. 4–6 Months β-carotene Treatment

| 1 | 282.66 |
|---|---|
| 2 | 582.53 |
| 3 | 73.80 |
| 4 | 245.32 |

Patient No. 5–9 months β-carotene Treatment

| 1 | 52.65 |
|---|---|
| 2 | 68.85 |
| 3 | 34.88 |
| 4 | 104.40 |

Patient No. 6–9 months β-carotene Treatment

| 1 | 43.53 |
|---|---|
| 2 | 46.99 |
| 3 | 30.80 |
| 4 | 77.53 |

Patient No. 7–9 months β-carotene Treatment

| 1 | 62.61 |
|---|---|
| 2 | 85.79 |
| 3 | 37.12 |
| 4 | 103.07 |

Patient No. 8–9 months β-carotene Treatment

| 1 | 124.03 |
|---|---|
| 2 | 415.24 |
| 3 | 69.96 |
| 4 | 340.22 |

Patient No. 9–9 months β-carotene Treatment

| 1 | 72.70 |
|---|---|
| 2 | 77.09 |
| 3 | 44.97 |
| 4 | 117.75 |

Patient No. 10–9 months β-carotene Treatment

| 1 | 65.58 |
|---|---|
| 2 | 71.08 |
| 3 | 55.65 |
| 4 | 95.22 |

As can be observed in Table 3, higher levels of the IME proteolytic activities were initially induced by β-carotene treatments but with continued treatments, the levels of proteolytic activities returned to normal levels. By 9 months of treatment with β-carotene, protease levels were at normal levels. The treatment regimens for oral leukoplakia with BBIC and β-carotene are different. BBIC is administered as a single dose while β-carotene is administered daily over a period of months. Despite these differences, it appears that both BBIC and β-carotene treatments are capable of leading to increased levels of proteolytic activities which serve as the IME in these studies.

β-carotene is about to be approved by the FDA for treatment of oral leukoplakia/erythroplakia as it is known to cause the regression/disappearance of the pre-malignant condition. The induction of proteases, which degrade tissue, is believed to be essential for the efficacy of the β-carotene therapy. It is, therefore, believed that the induction of the proteases is responsible for the disappearance of leukoplakia/erythroplakia in β-carotene treated tissue. BBIC appears to be having a similar effect in the treatment of leukoplakia/erythroplakia.

BBIC is useful as an agent to treat pre-malignant tissue (e.g., hyperplasia, metaplasia and dysplasia) in other organs as well. A patient with benign prostatic hyperplasia (BPH) was administered a composition comprising BBIC. BPH is a condition in which hyperplasia and hypertrophy of cells are present in the prostate gland. This pre-malignant condition is similar to oral leukoplakia in that both lesions represent hyperplastic and hypertrophic tissue. This condition leads to enlargement of the prostate gland resulting in problems during urination. BPH is a common problem in older men. During treatment with the BBIC composition, the patient claimed to have relief of the symptoms associated with difficulty in urination associated with BPH.

The following examples illustrate the practice of this invention and the characterization and utility of products resulting therefrom. They are provided for illustrative purposes only and are not intended to limit the invention.

EXAMPLES

Example 1

Preparation of Soybean Solubles

One hundred pounds of high-nitrogen-soluble (NSI 72—Nitrogen Solubility Index by A.O.C.S. Method) hexane-extracted soy flour (52%, protein—6.25 x N) were weighed into a 100 gallon agitated vessel containing 500 pounds of 60% aqueous 3A ethanol that was maintained at 135°±5° F. The resulting suspension was allowed to settle overnight. The supernatant was then transferred into a clean drum and filtered through a 5 micron bag filter. The filtrate was then adjusted to pH 5.3± 0.05 with 1.0N HCl. At this point, 1.8 pounds of acetone was added to each pound of filtrate in the kettle (432 pounds of acetone to 240 pounds of filtrate, without agitation) to precipitate the crude BBI active ingredient. The mix was then stirred mildly to assure uniformity. The precipitated solids were allowed to settle for one (1) hour. The supernatant was filtered through a 5 micron bag filter. The precipitate was scraped from the container walls and mixed with the filtered solids from the supernatant. The solids were then resolubilized with water using gentle agitation for 15 minutes at room temperature, and subjected to ultrafiltration in an OSMONICS™ Ultra-Filtration Unit (Osmonic Inc., Minnetonka, Minn.) using a 192T-PS (2,000 MW cut-off). The concentrated fraction containing the BBI was centrifuged and the resulting precipitate, comprising solid impurities, was discarded. The supernatant was freeze-dried. The yield was 525 g of soybean solubles with a Chymotrypsin Inhibitor (CI) level of 70.4 mgs/g.

Example 2

Preparation of purified BBI concentrate

A slurry comprising 139 pounds of soybean solubles from an acidic aqueous extraction of hexane-defatted soybeans and 332 pounds of water was prepared. The slurry of the diluted soybean solubles was centrifuged to remove insoluble matter, and the partially purified solids were further diluted with water to a 8% solids level. These purified soy solubles were then subjected to ultrafiltration using a 1,000 MW cut-off membrane at 15 gpm and 105 psig, until 31 gallons of permeate was collected. The remaining liquid, which contains the crude BBI concentrate, was again diluted with 31 gallons of water, and the ultrafiltration step was repeated until an additional 47 gallons of permeate was collected and 45 gallons of a semi-crude BBI concentrate remained.

Fifty-five gallons of acetone was then added to 25 gallons of the semi-crude BBI concentrate. The resulting precipitate, containing purified BBI concentrate, was allowed to settle for one hour. The liquid was then decanted, and the precipitate containing the purified BBI concentrate was placed in a Buchner Funnel under vacuum to draw off the excess liquid. The dried precipitate was ground in a Waring blender and reslurried to 15% solids. The reslurried suspension was then allowed to settle and the supernatant was lyophilized. The yield was 8 pounds of purified BBI concentrate with a CI level of 135.5 mgs/g.

Example 3

Preparation of purified BBI concentrate

A slurry comprising 87.3 pounds of soybean solubles from an acidic aqueous extraction of hexane-defatted soybeans and 207.5 pounds of water was prepared. The slurry was centrifuged to remove the insoluble sludge material; diluted to 8% solids with water; and then subjected to ultrafiltration over a 1,000 MW cut-off membrane at 15 gpm and 100 psig. Forty-four pounds of permeate was collected. The crude BBI concentrate was re-diluted with 44 pounds of water, and the ultrafiltration step was repeated. Permeate (112 pounds) and semi-crude BBI concentrate (163 pounds) were collected.

Acetone (270 pounds) was then added to this semi-crude BBI concentrate, and the precipitated BBI concentrate thus formed was allowed to settle for one hour. The liquid was decanted and the precipitate was placed in a Buchner funnel under vacuum to draw off the excess liquid. It was then reslurried with water in a Waring blender, allowed to settle, and the supernatant was spray-dried. The yield was 2.3 pounds of purified BBI concentrate with a CI content of 261 mgs/g.

Example 4

Preparation of purified BBI concentrate

Soybean solubles (90 pounds) from an acidic aqueous extraction of hexane-defatted soybeans were diluted to between 15% to 20% of solids with water. (The initial solubles contain 50–60% solids.) The slurry was centrifuged to remove any insoluble sludge (approximately 3–5% of solids). The supernatant solution was then diluted with water to 10% solids and subjected to ultrafiltration over a 1,000 MW cut-off membrane. One pound of high-purity water was added to the fraction containing the crude BBI concentrate for every one pound of permeate that was removed during ultrafiltration. The ultrafiltration was considered complete when the solids content in the permeate had begun to decrease. At that point, the BBI concentrate was spray-dried. The yield was 14 pounds of purified BBI concentrate with a CI content of 99.2 mgs/g.

Example 5

Preparation of purified BBI concentrate

A slurry comprising 50.2 pounds of soybean solubles from an acidic aqueous extraction of hexane-defatted soybeans and 126.2 pounds of water was prepared. The slurry was centrifuged to remove any insoluble sludge (approximately 3–5% of solids present]. The supernatant solution was then diluted with water to 10% solids and subjected to ultrafiltration over a 10,000 MW cut-off membrane. One pound of high-purity water was added to the concentrate fraction for every one pound of permeate that had been removed during ultrafiltration. When the solids content had begun to decrease in the permeate, the permeate was also subjected to ultrafiltration over a 1,000 MW cut-off membrane. The fraction containing the BBI concentrate was then spray-dried. The yield was 2.6 pounds of purified BBI concentrate with a CI content of 61.9 mgs/g.

Example 6

Preparation of purified BBI concentrate

A slurry obtained from the whey protein stream produced during the production of soy protein isolate was treated by ultrafiltration over a 1,000 MW cut-off membrane, as described in Example 4. A total of 157.75 pounds of whey protein solution was used. After ultrafiltration, the BBI concentrate fraction, containing 2.7% solids, was spray-dried. The yield was 1.2 pounds of purified BBI concentrate, containing 187.8 mgs/g of CI.

Example 7

Soy solubles (1,000 grams) with a solids content of 19%, obtained from an acidic aqueous extraction of hexane-defatted soybeans, were centrifuged to remove insoluble matter. Two liters of acetone were added to the resulting supernatant. The resulting precipitate containing partially purified BBI concentrate was allowed to settle for one hour. The liquid was then decanted. The precipitate containing the partially purified BBI was then resuspended in 200 ml of water and centrifuged to remove matter rendered irreversibly insoluble by acetone. Acetone (400 ml) was added to the resulting supernatant. The water soluble, acetone insoluble precipitate which was formed was allowed to settle for one hour. The supernatant was decanted. Most of the water remaining in the precipitate was removed by resuspending the precipitate in 100 ml of acetone and allowing the precipitate to settle for 30 minutes. The supernatant was decanted. The BBI concentrate precipitate was spread thinly on a tray and allowed to air dry to a free flowing white powder. The yield was 5 gm of purified BBI concentrate having a CI level of 200 mgs/g.

Example 8

C3H10T1/2 cell transformation assay

The C3H10T1/2 cell transformation assay system was the in vitro system in which BBI was first identified as an anticarcinogenic agent. Therefore, the C3H10T1/2 cell transformation assay was used for in vitro transformation studies to evaluate the anticarcinogenic activity of BBIC compositions of the present invention. C3H10T1/2 cells are a mouse embryo fibroblast cell line which can be transformed in culture by chemicals and radiation. When transformed, the cells pile up, forming densely staining foci against a background monolayer of contact-inhibited cells. The transformed foci are characterized as type II or type III using defined morphological criteria. A very high percentage of type II and III foci are tumorigenic when inoculated into syngeneic or nude mice.

To assay for the inhibition of oncogenic transformation by extracts of soybeans, in the in vitro assay the following protocol is employed: C3H10T1/2 cells are seeded and after 24 hours, treated with 600 R of radiation. Immediately after carcinogen treatment, the medium is changed to complete medium containing the sample of interest (at the highest non-toxic level to at most 1 mM; in previous studies it was observed that if compounds do not have an effect at this concentration (1 mM) in the medium they will not have an effect at higher levels). Subsequently, the medium is changed at weekly intervals. At 6 weeks the dishes are fixed and stained, and the transformed foci evaluated.

When a new composition, such as the BBIC compositions taught in the instant application, proves positive in inhibiting transformation in vivo, it is tested for the ability to inhibit carcinogenesis in vivo. The in vivo test used was inhibition of 7,12-dimethylbenz[a]anthracene-induced oral carcinogenesis in hamsters (see Example 9).

Example 9

7,12-dimethylbenz[a]anthracene-induced oral carcinogenesis in hamsters

Non-inbred male Syrian hamsters, 4 weeks old and weighing 70–90 grams were obtained from Charles River Breeding Laboratories, Wilmington, Mass. The animals were housed 4 per cage with wood chips for bedding. The environment was controlled with an alternating 12-hour light-dark cycle. Water and Purina Laboratory Chow (#5001; Ralston Purina Co., St. Louis, Mo.) were available ad libitum. The hamsters were divided into 23 groups, 3 groups containing 4 animals each, and 20 groups containing 8 animals each (plus one extra animal in Group 17).

Three groups of 4 animals each were treated as follows ("0" time represents the beginning of DMBA treatments):

Group 1—1% BBI 5 times per week for 0–180 days.
Group 2—1% PBBI 5 times per week for 0–180 days.
Group 3—Mineral oil 3 times per week for 0–60 days.

These groups served as controls for the other experimental groups whose treatments are described below:

Group 4—DMBA 3 times per week for 0–60 days.
Group 5—DMBA 3 times per week for 0–60 days+1% BBI 5 times per week for 0–180 days.
Group 6—DMBA 3 times per week for 0–60 days+1% BBIC (prepared as described in Example 2) 5 times per week for 0–180 days.
Group 7—DMBA 3 times per week for 0–60 days+1% BBI 30 times per week for 0–180 days.
Group 8—DMBA 3 times per week for 0–60 days+1% BBI 1 time per week for 0–180 days.
Group 9—DMBA 3 times per week for 0–60 days+1% BBI 5 times per week for 0–60 days.
Group 10—DMBA 3 times per week for 0–60 days+1% BBI 5 times per week for 0–90 days.
Group 11—DMBA 3 times per week for 0–60 days+1% BBI 5 times per week for 14–90 days.
Group 12—DMBA 3 times per week for 0–60 days+1% BBI 5 times per week for 45–135 days.
Group 13—DMBA 3 times per week for 0–60 days+1% BBI 5 times per week for 90–180 days.
Group 14—DMBA 3 times per week for 0–60 days+0.1% BBIC (prepared as described in Example 2) 5 times per week for 0–180 days.
Group 15—DMBA 3 times per week for 0–60 days+0.01% BBI 5 times per week for 0–180 days.
Group 16—DMBA 3 times per week for 0–60 days+0.001% BBI 5 times per week for 0–180 days.
Group 17—DMBA 3 times per week for 0–60 days+1% PBBI 5 times per week for 0–180 days.
Group 18—DMBA 3 times per week for 0–60 days+0.1% PBBI 5 times per week for 0–180 days.
Group 19—DMBA 3 times per week for 0–60 days+0.01% PBBI 5 times per week for 0–180 days.
Group 20—DMBA 3 times per week for 0–60 days+0.001% PBBI 5 times per week for 0–180 days.
Group 21—DMBA 3 times per week for 0–60 days+1% PBBI 3 times per week for 0–180 days.
Group 22—DMBA 3 times per week for 0–60 days+1% PBBI 1 time per week for 0–180 days.
Group 23—DMBA 3 times per week for 0–60 days+1% Potato Inhibitor 5 times per week for 0–180 days.

All treatments were applied topically to the right cheek pouch. Animals were weighed at weekly intervals. DMBA (Sigma Chemical Co., St. Louis, Mo.) was applied in a 0.25% solution in heavy mineral oil (U.S.P.) at a dose of 0.125 mg on the cheek pouch 3 times per week for 8 weeks of treatment (i.e., 0.375 mg/wk). This is a standard protocol for DMBA-induced hamster cheek pouch carcinogenesis.

Several preparations of protease inhibitors were used in the studies reported here. BBI is an extract of the inhibitor, "BBI concentrate", that has been described in detail elsewhere (Yavelow et al., 1985) and was prepared by Central Soya Company, Inc. (Ft. Wayne, Ind.). The extract contains five separate protease inhibitors all of which are very similar to BBI in molecular weight and trypsin inhibitory activity. The BBI extract was dissolved in distilled water at a final concentration of 0.001–1.0%. BBIC, prepared as described in Example 2 herein, was also supplied by Central Soya. PBBI containing BBI which has been purified to near homogeneity and is greater than 95% pure BBI, was prepared from the "BBI concentrate" as previously described (Yavelow et al. 1985). The Potato Inhibitor extract (Kemin Product No. 068129), enriched in Chymotrypsin Inhibitor I from potatoes (70% of the extract is the inhibitor), was prepared by Kemin Industries, Inc.

All animals were treated for 20 weeks and then sacrificed by $CO_2$ inhalation. The time between the last application of DMBA and animal sacrifices was approximately 4 months. At the time of autopsy, all organs were examined and any organs having an abnormal appearance were removed for histopathologic analysis. The location of all tumors was noted and the size in millimeters was recorded. The cheek pouches were carefully examined, photographed and then prepared for histopathologic analysis. Each pouch was fixed in 10% buffered formalin and embedded in paraffin. Five-micron sections were cut and stained with hematoxylin and eosin.

For each animal of each treatment group, the results of the cheek pouch histopathologic analysis are shown in Table 1. Histopathological alterations observed in organs other than the cheek pouch are also given in Table 4. The data for the tumors of the cheek pouch (given in Table 4) are shown in histogram form in FIG. 1. Examples of hamster cheek pouches with and without tumors are shown in FIG. 2(a) and FIG. 2(b).

TABLE 4

Histopathologic Alterations Observed in the Animals[1,2,3]

| Group/Treatment | Animal No. | Premalignant Lesions: Animals having: Single focus of hyperplasia | Multiple loci of hyperplasia | Papillary hyperplasia | Tumors: Number of tumors (per animal) Sebaceous gland adenomas | Papillomas | Squamous cell carcinomas (i = invasive) | Total tumors (per animal) | Average number of tumors/ animal = Mean ± Standard Error |
|---|---|---|---|---|---|---|---|---|---|
| 1-1% BBI | 1 | 0 | 0 | 0 | 0 | 0 | 0 | 0 | |
|  | 2 | 0 | 0 | 0 | 0 | 0 | 0 | 0 | 0 |
|  | 3 | 0 | 0 | 0 | 0 | 0 | 0 | 0 | |
|  | 4 | 0 | 0 | 0 | 0 | 0 | 0 | 0 | |
| 2-1% PBBI | 1 | .0 | 0 | 0 | 0 | 0 | 0 | 0 | |
|  | 2 | 0 | 0 | 0 | 0 | 0 | 0 | 0 | 0 |
|  | 3 | 0 | 0 | 0 | 0 | 0 | 0 | 0 | |
|  | 4 | 0 | 0 | 0 | 0 | 0 | 0 | 0 | |
| 3-Mineral Oil | 1 | 0 | 0 | 0 | 0 | 0 | 0 | 0 | |
|  | 2 | 0 | 0 | 0 | 0 | 0 | 0 | 0 | 0 |
|  | 3 | 0 | 0 | 0 | 0 | 0 | 0 | 0 | |
|  | 4 | 0 | 0 | 0 | 0 | 0 | 0 | 0 | |
| 4-DMBA 3x/wk (0-60d) | 1 | 0 | 0 | 0 | 0 | 1 | 5 (i) | 6 | |
|  | 2 | 0 | 0 | 0 | 0 | 2 | 4 (i) | 6 | |
|  | 3 | 0 | 0 | 0 | 0 | 0 | 1 (i) | 1 | |
|  | 4 | x (squamous) | 0 | 0 | 0 | 0 | 0 | 0 | 2.7 ± 0.9 |
|  | 5 | 0 | 0 | 0 | 0 | 0 | 1 | 1 | |
|  | 6 | 0 | x | 0 | 0 | 1 | 1 (i) | 2 | |
|  | 7 | 0 | 0 | 0 | 0 | 0 | 3 (i) | 3 | |
| 5-DMBA + BBI-1% 5x/wk (0-180d) | 1 | 0 | 0 | 0 | 0 | 0 | 2 (i) | 2 | |
|  | 2 | 0 | 0 | 0 | 0 | 1 | 0 | 1 | |
|  | 3 | 0 | 0 | 0 | 0 | 2 (squamous) | 0 | 2 | |
|  | 4 | 0 | 0 | 0 | 0 | 0 | 0 | 0 | 0.6 ± 0.4 |
|  | 5 | 0 | 0 | 0 | 0 | 0 | 0 | 0 | |
|  | 6 | 0 | 0 | 0 | 0 | 0 | 0 | 0 | |
|  | 7 | 0 | 0 | 0 | 0 | 0 | 0 | 0 | |
|  | 8 | 0 | 0 | 0 | 0 | 0 | 0 | 0 | |
| 6-DMBA + BBIC-1% 5x/wk (0-180d) | 1 | 0 | x (squamous) | 0 | 0 | 0 | 0 | 0 | |
|  | 2 | 0 | 0 | 0 | 0 | 1 | 0 | 1 | |
|  | 3 | 0 | 0 | 0 | 1 | 0 | 0 | 1 | |
|  | 4 | 0 | 0 | 0 | 0 | 0 | 0 | 0 | 0.3 ± 0.2 |
|  | 5 | 0 | 0 | 0 | 0 | 0 | 0 | 0 | |
|  | 6 | 0 | 0 | 0 | 0 | 0 | 0 | 0 | |
|  | 7 | 0 | 0 | 0 | 0 | 0 | 0 | 0 | |
| 7-DMBA + BBI-1% 3x/wk (0-180d) | 1 | 0 | x | 0 | 0 | 0 | 0 | 0 | |
|  | 2 | x | 0 | 0 | 0 | 0 | 0 | 0 | |
|  | 3 | 0 | x | 0 | 0 | 0 | 1 | 1 | |
|  | 4 | 0 | 0 | 0 | 0 | 0 | 1 (i) | 1 | |
|  | 5 | 0 | 0 | 0 | 0 | 1 | 1 | 2 | 0.6 ± 0.3 |
|  | 6 | 0 | 0 | 0 | 0 | 0 | 0 | 0 | |
|  | 7 | 0 | 0 | 0 | 0 | 0 | 0 | 0 | |
| 8-DMBA + BBI - 1% 1x/wk (0-180d) | 1 | 0 | 0 | x | 0 | 1 | 1 (i) | 2 | |
|  | 2 | 0 | 0 | 0 | 1 | 0 | 1 (i) | 2 | |
|  | 3 | 0 | 0 | 0 | 0 | 0 | 1 | 1 | |
|  | 4 | 0 | 0 | 0 | 0 | 0 | 0 | 0 | |
|  | 5 | 0 | 0 | 0 | 0 | 0 | 0 | 0 | 0.6 ± 0.3 |
|  | 6 | 0 | 0 | 0 | 0 | 0 | 0 | 0 | |
|  | 7 | 0 | 0 | 0 | 0 | 0 | 0 | 0 | |
|  | 8 | 0 | 0 | 0 | 0 | 0 | 0 | 0 | |
| 9-DMBA + BBI-1% 5x/wk (0-60d) | 1 | 0 | 0 | x | 0 | 0 | 0 | 0 | |
|  | 2 | 0 | 0 | x (squamous) | 0 | 0 | 0 | 0 | |
|  | 3 | 0 | 0 | 0 | 0 | 0 | 11 (i) | 11 | |
|  | 4 | 0 | 0 | 0 | 0 | 0 | 0 | 0 | 1.8 ± 1.8 |
|  | 5 | 0 | 0 | 0 | 0 | 0 | 0 | 0 | |
|  | 6 | 0 | 0 | 0 | 0 | 0 | 0 | 0 | |
| 10-DMBA + BBI-1% 5x/wk (0-90d) | 1 | 0 | x | 0 | 0 | 0 | 0 | 0 | |
|  | 2 | 0 | x | 0 | 0 | 0 | 0 | 0 | |
|  | 3 | 0 | 0 | 0 | 0 | 0 | 1 (i) | 1 | |
|  | 4 | 0 | 0 | 0 | 0 | 0 | 1 | 1 | 0.3 ± 0.2 |
|  | 5 | 0 | 0 | 0 | 0 | 0 | 0 | 0 | |
|  | 6 | 0 | 0 | 0 | 0 | 0 | 0 | 0 | |
|  | 7 | 0 | 0 | 0 | 0 | 0 | 0 | 0 | |
| 11-DMBA + BBI-1% | 1 | x | 0 | 0 | 0 | 0 | 1 | 1 | |
|  | 2 | 0 | 0 | 0 | 0 | 1 | 0 | 1 | |

TABLE 4-continued

Histopathologic Alterations Observed in the Animals[1,2,3]

| Group/Treatment | Animal No. | Premalignant Lesions: Animals having: | | | Tumors: Number of tumors (per animal) | | | Total tumors (per animal) | Average number of tumors/ animal = Mean ± Standard Error |
|---|---|---|---|---|---|---|---|---|---|
| | | Single focus of hyperplasia | Multiple loci of hyperplasia | Papillary hyperplasia | Sebaceous gland adenomas | Papillomas | Squamous cell carcinomas (i = invasive) | | |
| 5x/wk | 2 | 0 | 0 | 0 | 0 | 0 | 0 | 0 | |
| (14-90d) | 4 | 0 | 0 | 0 | 0 | 0 | 0 | 0 | |
| | 5 | 0 | 0 | 0 | 0 | 0 | 0 | 0 | 0.3 ± 0.2 |
| | 6 | 0 | 0 | 0 | 0 | 0 | 0 | 0 | |
| | 7 | 0 | 0 | 0 | 0 | 0 | 0 | 0 | |
| 12-DMBA + | 1 | 0 | 0 | 0 | 0 | 1 | 0 | 1 | |
| BBI-1% | 2 | 0 | 0 | 0 | 0 | 0 | 1 | 1 | |
| 5x/wk | 3 | 0 | 0 | x | 0 | 0 | 1 | 1 | |
| (45-135d) | 4 | 0 | 0 | 0 | 0 | 0 | 0 | 0 | |
| | 5 | 0 | 0 | 0 | 0 | 0 | 0 | 0 | 0.4 ± 0.2 |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 13-DMBA + | 1 | x | 0 | 0 | 0 | 0 | 0 | 1 | |
| BBI-1% | 2 | 0 | 0 | x | 0 | 1 | 0 | 1 | |
| 5x/wk | 3 | 0 | 0 | x (squamous) | 0 | 0 | 2 (i) | 2 | |
| (90-180d) | 4 | 0 | 0 | 0 | 0 | 0 | 0 | 0 | 0.7 ± 0.3 |
| | 5 | 0 | 0 | 0 | 0 | 0 | 0 | 0 | |
| | 6 | 0 | 0 | 0 | 0 | 0 | 0 | 0 | |
| 14-DMBA + | 1 | 0 | 0 | 0 | 0 | 0 | 0 | 0 | |
| BBIC-0.1% | 2 | x | 0 | 0 | 0 | 3 | 0 | 3 | |
| 5x/wk | 3 | 0 | 0 | x | 0 | 0 | 0 | 0 | |
| (0-180d) | 4 | x | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 15-DMBA + | 1 | 0 | 0 | 0 | 0 | 1 | 0 | 1 | |
| BBI-0.01% | 2 | 0 | x | 0 | 1 | 1 | 0 | 2 | |
| 5x/wk | 3 | 0 | 0 | 0 | 0 | 0 | 0 | 0 | |
| (0-180d) | 4 | 0 | 0 | 0 | 0 | 0 | 1 | 1 | 0.6 ± 0.3 |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 16-DMBA + | 1 | 0 | 0 | 0 | 0 | 0 | 4 (i) | 4 | |
| BBI-0.001% | 2 | x | 0 | 0 | 0 | 0 | 0 | 0 | |
| | 3 | 0 | 0 | 0 | 1 | 0 | 0 | 1 | |
| 5x/wk | 4 | 0 | 0 | 0 | 0 | 1 | 0 | 1 | |
| (0-180d) | 5 | 0 | 0 | 0 | 0 | 0 | 0 | 0 | 0.9 ± 0.6 |
| | 6 | 0 | 0 | 0 | 0 | 0 | 0 | 0 | |
| | 7 | 0 | 0 | 0 | 0 | 0 | 0 | 0 | |
| 17-DMBA + | 1 | 0 | 0 | x | 0 | 0 | 1 | 1 | |
| PBBA-1% | 2 | 0 | 0 | 0 | 0 | 0 | 0 | 0 | |
| 5x/wk | 3 | 0 | 0 | 0 | 0 | 0 | 1 | 1 | |
| (0-180d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | 0.2 ± 0.2 |
| | 7 | 0 | 0 | 0 | 0 | 0 | 0 | 0 | |
| | 8 | 0 | 0 | 0 | 0 | 0 | 0 | 0 | |
| | 9 | 0 | 0 | 0 | 0 | 0 | 0 | 0 | |
| 18-DMBA + | 1 | x | 0 | 0 | 0 | 0 | 0 | 0 | |
| PBBI-0.1% | 2 | x (squamous) | 0 | 0 | 0 | 0 | 0 | 0 | |
| 5x/wk | 3 | 0 | x | 0 | 0 | 0 | 3 (i) | 0 | |
| (0-180d) | 4 | 0 | 0 | 0 | 1 | 0 | 0 | 4 | |
| | 5 | 0 | x | 0 | 0 | 0 | 0 | 0 | 0.5 ± 0.5 |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 19-DMBA + | 1 | 0 | 0 | 0 | 0 | 0 | 3-papillary (i) | 3 | |
| PBBI-0.01% | 2 | 0 | 0 | 0 | 0 | 0 | 0 | 0 | |
| | 3 | 0 | 0 | 0 | 0 | 0 | 0 | 0 | |
| 5x/wk | 4 | 0 | 0 | 0 | 0 | 0 | 0 | 0 | 0.3 ± 0.2 |
| (0-180d) | 5 | 0 | 0 | 0 | 0 | 0 | 0 | 0 | |
| | 6 | 0 | 0 | 0 | 0 | 0 | 1 (i) | 1 | |
| | 7 | 0 | 0 | 0 | 0 | 0 | 0 | 0 | |
| 20-DMBA + | 1 | 0 | x | 0 | 0 | 0 | 0 | 0 | |
| PBBI-0.001% | 2 | 0 | 0 | 0 | 0 | 0 | 6 (i) | 6 | |
| | 3 | 0 | x | 0 | 0 | 2 | 3 (i) | 5 | |

TABLE 4-continued

Histopathologic Alterations Observed in the Animals[1,2,3]

| Group/Treatment | Animal No. | Premalignant Lesions: Animals having: | | | Tumors: Number of tumors (per animal) | | | | Average number of tumors/animal = |
|---|---|---|---|---|---|---|---|---|---|
| | | Single focus of hyperplasia | Multiple loci of hyperplasia | Papillary hyperplasia | Sebaceous gland adenomas | Papillomas | Squamous cell carcinomas (i = invasive) | Total tumors (per animal) | Mean ± Standard Error |
| 5x/wk | 4 | 0 | 0 | 0 | 0 | 0 | 0 | 0 | 1.6 ± 1.0 |
| (0-180d) | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 21-DMBA + | 1 | 0 | x | 0 | 0 | 0 | 0 | 0 | |
| PBBI-1% | 2 | 0 | 0 | 0 | 1 | 0 | 1 | 2 | |
| 3x/wk | 3 | 0 | 0 | 0 | 1 | 0 | 1 | 2 | |
| (0-180d) | 4 | 0 | 0 | 0 | 0 | 0 | 0 | 0 | 0.6 ± 0.4 |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 22-DMBA + | 1 | x | 0 | 0 | 0 | 1 | 1 | 2 | |
| PBBI-1% | 2 | 0 | 0 | x | 0 | 0 | 0 | 0 | |
| 1x/wk | 3 | 0 | 0 | 0 | 0 | 1 | 0 | 1 | 0.5 ± 0.3 |
| (0-180d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 23-DMBA + | 1 | 0 | 0 | 0 | 0 | 1 | 1 (i) | 2 | |
| Pot. Inh. | 2 | 0 | 0 | 0 | 1 | 0 | 1 | 2 | |
| -1% | 3 | 0 | 0 | 0 | 0 | 0 | 1 | 1 | 1.4 ± 0 |
| 5x/wk | 4 | 0 | 0 | 0 | 0 | 0 | 1 | 1 | |
| (0-180d) | 5 | 0 | 0 | 0 | 0 | 0 | 1 (i) | 1 | |

Abbreviations used in Table 4 include BBI which refers to an extract of the inhibitor, "BBI concentrate" that has been, described in detail elsewhere (Yavelow et al., 1985) and was prepared by Central Soya Company, Inc. (Ft. Wayne, Ind.). The extract contains five separate protease inhibitors all of which are very similar to BBI in molecular weight and trypsin inhibitory activity. The BBI extract was dissolved in distilled water at a final concentration of 0.001–1.0%. BBIC refers to a product of the present invention, prepared as described in Example 2 herein, also supplied by Central Soya. PBBI refers to a composition containing BBI which has been purified to near homogeneity and is greater than 95% pure BBI, prepared from the "BBI concentrate" as previously described (Yavelow et al. 1985).

Other pathological conditions were observed in several of the treatment groups. In Group 4, animal 2 had a hyperplastic spleen. In Group 9, animal 3 also had a hyperplastic spleen. In Group 12, animal 5 suffered from kidney nephrosis. In Group 14, animal 1 had stomach, squamous papillary hyperplasia. In Group 16, animal 4 had a melanin nodule. In Group 18, animal 6 had a leukemic node and in Group 21, animal 7 had stomach papillomas and a lymphoreticular tumor.

Figure 2A:
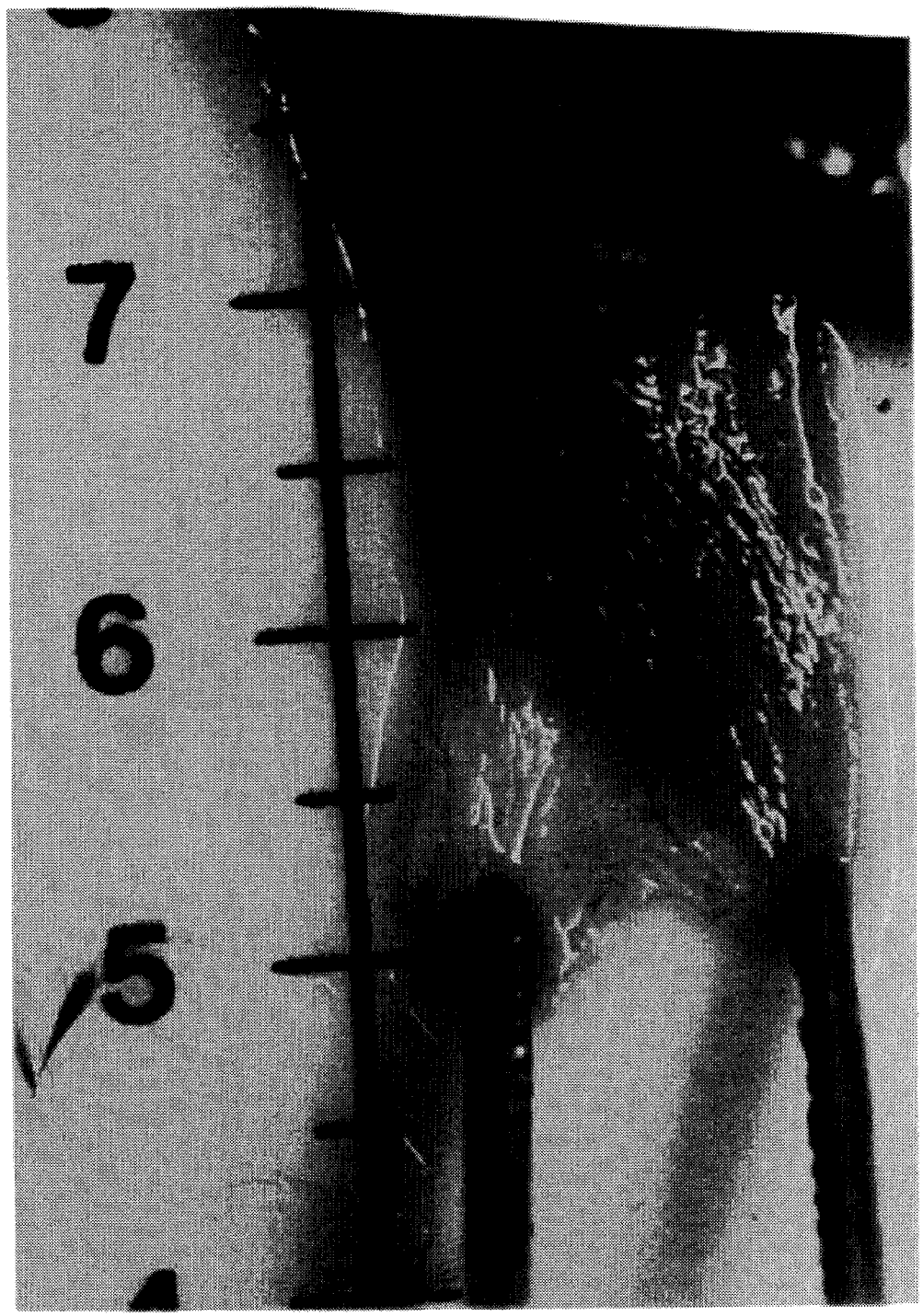
FIG. 2(a) is a photograph of a normal (untreated) hamster cheek pouch.
Figure 2B:
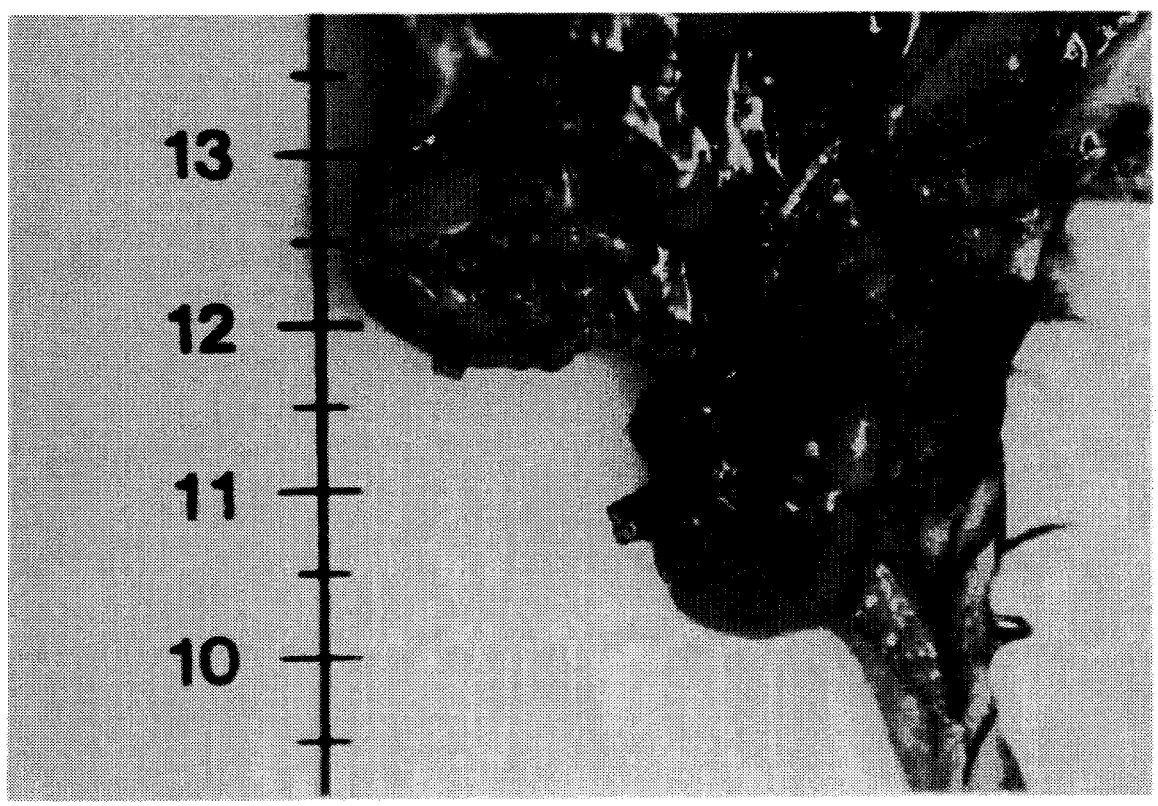
FIG. 2(b) is a photograph showing a DMBA-treated hamster cheek pouch with tumors.

The conclusions that can be drawn from the data shown in Table 4 and FIG. 1 are as follows:

1) When present for the entire carcinogenesis assay period (0–180 days), BBI significantly suppresses DMBA-induced oral carcinogenesis at concentrations from 1% down to 0.01% (Groups 4 vs. 5, 6, 14 and 15, $p<0.05$). At 0.001%, the suppression of carcinogenesis by BBI is not statistically significant (Group 4 vs. 16, $p>0.05$).

2) 1% BBI applications at 5 times per week, 3 times per week and once per week (for the entire carcinogenesis assay period, 0–180 days), led to a significant reduction in the DMBA-induced tumor yield (Groups 4 vs. 5, 7 and 8, $p<0.05$).

3) 1% BBI applications for the following time periods led to a significantly reduced tumor yield: 0–180 days, 0–90 days, 14–90 days and 45–135 days (Groups 4 or 5, 6, 10 and 11, $p<0.05$). Application of 1% BBI from days 0–60 and 90–180 reduced the DMBA-induced tumor yield but not in a statistically significant manner (Groups 4 vs. 9, $p>0.5$; Groups 4 vs. 13, $p<0.10$).

4) BBIC, prepared as described in Example 2, gave results similar to those obtained for the previous method of preparing BBI (at 1% BBI) when applied 5 times per week for 0–180 days; both the BBI prepared by the previous method and the BBIC composition of the present invention led to a significant reduction in the DMBA-induced tumor yield (Groups 4 vs. 5, $p<0.05$; 4 vs. 6, $p<0.02$). The composition of the present invention, however, was more effective than the BBI composition prepared by the standard method, as the results were of higher statistical significance, and no malignant tumors were observed with this preparation (squamous cell carcinomas were observed in the animals treated with the standard BBI preparation).

The histopathological analysis showed that there were tumors in all of the experimental groups receiving DMBA treatments. The only DMBA+BBI groups in which no animals had malignant tumors were the groups receiving the BBIC composition of the present invention (specifically, Group 6 and Group 14). The fact that BBIC can suppress oral carcinogenesis, when given long periods after exposure to the carcinogen in these experiments, suggests that BBIC is capable of destroying pre-malignant and malignant cells present in the tissue of the animals.

Example 10

Human Clinical Study Protocol

The BBI Concentrate (BBIC) from soybeans was supplied from Central Soya as a fine powder, C.I. activity=100 mg/g.

The BBIC is administered as a mouthwash. This product is designed to be a stable mouthwash solution that provides extended mucosal contact time, is palatable, easy to administer and suitable for low cost mass production. A saliva substitute provides the solution with the necessary viscosity to increase mucosal contact time and bioavailability, and has been shown to provide sustained release of many compounds. In the formulation prepared for these experiments, BBI Concentrate (BBIC), the "saliva substitute" (Roxane Laboratories, Inc. Columbus, Ohio) and water are included.

In single dose studies, 100 C.I. units BBIC in 20 ml of the mouthwash solution (14 ml saliva substitute+6 ml water) was employed.

Other doses to be studied include 25 C.I. units BBIC, and 200 and 400 C.I units. These latter doses will yield data on toxicity at higher doses and any dose-dependent alteration in pharmacokinetics. During the pharmacokinetic studies, each dose group is completely studied before the next tier on the dose escalation regime is enrolled. Evidence for clinical, hematological, renal or hepatological toxicity is searched for in each group of subjects. Dose escalations do not proceed if any subject develops clinical or laboratory evidence of toxicity (i.e., Grade 1 toxicity). The only exception to this precondition would be the rare idiosyncratic allergic skin reaction.

For the oral bioavailability study, there are six subjects at each dose level. These subjects are required to provide buccal mucosal cells at different time points for the same dose level of BBI. As the limit of BBI solubility is slightly above 5 mg/ml, 25 C.I. units (containing 25 mg BBI) dissolves easily in the 20 ml volume to be utilized. A 20 ml volume is also utilized for the 100 C.I. unit dose. For the 200 and 400 C.I. unit doses, larger volumes of mouthwash are necessary to be sure that the C.I. activity is dissolved. For the 200 C.I. unit dose, a 40 ml mouthwash volume (28 ml saliva substitute+12 ml water) is utilized; and for the 400 C.I. unit dose, an 80 ml mouthwash volume (56 ml saline substitute 24 ml water) is utilized.

The dose of 100 C.I. units (100 mg C.I. activity) was chosen for the single dose studies, as it is planned that long-term, multiple dose studies will need approximately this dose to serve as a human cancer chemopreventive agent. This dose of protease inhibitor activity is sufficiently low that it should pose no health risk to patients. To calculate the protease inhibitor (P.I.) activity of BBIC, the number of C.I. units needs to be added to the number of trypsin inhibitor (T.I.) units. A 100 C.I. unit sample of BBIC contains 40 T.I. units, or a total of 140 P.I. units. 100 C.I. units/day, or 140 P.I. units/day, is the dose planned for the multiple dose study. As this dose is well within the amount of proteolytic activity contained in the normal Western diet for all sources of P.I. activity, and well within the amount contained in the normal Japanese diet from soybean protease inhibitors, there should be no health risks associated with the protocol.

Example 11

Administration of Mouthwash

Each 20 milliliter dose will be supplied to the research subjects in two separate containers. Each 2 ounce bottle will contain 14 milliliters of Saliva Substitute and 6 milliliters of water. BBIC (25 and 100 C.I.) will be provided in a separate container, for admixture prior to administration. The 200 and 400 unit doses will be administered in the 40 ml and 80 ml mouthwash volumes, as described in detail above.

Immediately after mixing the components and shaking the suspension for 30 seconds, each subject will self-administer the full 20 milliliters (or 40 or 80 ml) of mouthwash, swish for 1 minute and then swallow. Each subject will be required to drink 6 oz. of water after administration of BBIC to aid with gastrointestinal absorption. It is planned that the mouthwash will be taken within a few minutes of being mixed. It has been determined that the mouthwash is stable, in terms of C.I. activity, for a 3 hour period. Therefore, the mouthwash is used within a 3 hour period.

Example 12

Collection of Blood Samples

A heplock is inserted into vein in the right or left forearm of the patient. Prior to administration of BBIC, a base-line (zero time) blood sample is withdrawn through the intravenous line.

After administration of a BBIC composition, subsequent blood samples are drawn at 10, 15, 20 and 40 minutes and 1, 2, 3, 6, 12, 24 and 48 hours. Blood is drawn from the heplock line, with the initial 3 cc of blood being discarded. After collection of the blood sample, the plasma is separated and stored in a glass container at −20° C. until analysis.

Example 13

Collection of Buccal Mucosal Cells

After rinsing the mouth twice with tap water, the oral buccal mucosa is brushed lightly with a soft toothbrush. For collections of samples representative of the entire mouth, all surfaces are brushed. For collections from diseased or normal areas only, the brushing is confined to the appropriate side or lesion. The mouth and toothbrush are then rinsed with 30 ml of room temperature phosphate buffered saline (PBS), and the rinse is collected into a 50 ml centrifuge tube. The cells are filtered through cheesecloth, centrifuged and resuspended in PBS. Approximately 1 to 5 million cells can be easily and comfortably collected in this manner.

There are six subjects at each dose level providing oral mucosal cells. At each dose, one subject provides baseline (zero time cells), the second, third, fourth, fifth and sixth subjects provide the 1 hour, 6 hour, 12 hour, 24 hour and 48 hour buccal mucosal cells. Immediately after collection, the oral mucosal cells are frozen for determination of intracellular BBIC levels and intermediate marker studies at a later date.

Example 14

Analysis of Blood Samples

The concentration of BBIC present in blood samples taken at various time points following administration of the mouthwash is determined. Serum samples are analyzed for BBIC by a sandwich ELISA assay. This technique uses monoclonal antibodies to the BBI (anti-BBI-AB) which are highly specific for native BBI, as well as BBI complexed with proteases such as trypsin and chymotrypsin and BBIC. Aliquots of serum are placed in wells along with anti-BBI-AB. The amount of bound anti-BBI-AB is determined by adding a second antibody, horseradish peroxidase (HRP) rabbit anti-mouse IgG. HRP activity is assayed in citrate buffer (pH 4.2) containing 6.7 mM $H_2O_2$ and 1 mM 2,2'-azinobis-3-ethylbenzthiazolinesulfonic acid (ABTS). The reaction is stopped by adding 10% sodium dodecyl sulfate solution. The quantitation is performed by reading the absorbance of each well at 414 nm. A pharmacokinetic profile showing absorption and elimination of BBIC in serum is then generated. Pharmacokinetic parameters such as elimination rate constant (Ke), half-life (t1/2), volume of distribution (Vd) and area-under-the-curve (AUC) are then be obtained. These pharmacokinetic parameters at the different dose-levels are compared to check for any dose-dependent alterations.

Example 15

Analysis of Buccal Mucosa Samples

The buccal mucosa cells are analyzed for BBIC content by the sandwich ELISA assay as described above. Using the anti-BBI-AB, BBI concentration in cells previously treated with BBIC and growing in tissue culture are detected. Plastic microtiter dishes are coated with BBI. Oral epithelial cells are obtained and homogenized by sonication. Aliquots from homogenized cell samples are then placed in the wells along with anti-BBI-AB. The amount of anti-BBI-AB binding to the plate is determined by adding a second antibody (HRP-rabbit anti-mouse IgG). HRP activity is assayed in citrate buffer (pH 4.2) containing 6.7 mM $H_2O_2$ and 1 mM 2,2'azinobis (3-ethylbenzthiazolinesulfonic acid). The quantitation is performed by reading the absorbance of each well at 414 nm. These studies determine the uptake in BBIC in human buccal mucosa cells.

Levels of proteolytic activity in cells of leukoplakia patients who have or have not been exposed to the BBIC mouthwash are determined and compared to levels in control cells (from patients who have or have not been exposed to the BBIC mouthwash). Preliminary data showing that levels of proteolytic activity are elevated in cells of patients with leukoplakia (compared to control cells) indicates that this is and acceptable intermediate marker for oral carcinogenesis.

Example 16:

Measurement of Proteolytic Activity

Buccal mucosa cell samples are stored at $-70°$ C. until the enzyme assays are performed. The samples are homogenized in 0.1M Tris buffer (pH 7.0) at 4° C. and centrifuged at 5,000× g at 4° C. The supernatant fraction is used as the source of protease activity. One hundred microliter aliquots are assayed for protease activity with the protease substrates Boc-Val-Pro-Arg-MCA, Pyr-Gly-Arg-MCA and Suc-Ala-Ala-Pro-Phe-MCA (the protease substrates are prepared as 1 mg/ml stock solutions in DMSO). The reactions are performed in 100 mM Tris buffer (pH 7.0) containing 5 mM $MgCl_2$ for 30 minutes at 37° C. The reactions are terminated by boiling (1 minute boiling water bath). The release of the fluorescent reporter group AMC (amino-methyl-coumarin) is determined spectrofluorometrically at excitation and emission wavelength of 380/460 nm, respectively. The spectrofluorometer is standardized such that $10^{-7}M$ AMC=700 fluorescent units. Protein concentrations are determined using bovine serum albumin as standard. The specific activity of these proteases is compared in the different samples of buccal cells from patients.

Example 17

Treatment of Benign Prostatic Hyperplasia

A patient suffering from benign prostatic hyperplasia was administered BBIC pills (100 C.I. units) daily for 8 days. Benign prostatic hyperplasia (BPH) is a condition in which hyperplasia and hypertrophy of cells are present in the prostate gland. This condition leads to enlargement of the prostate gland which in turn leads to problems in urination. BPH is associated with high levels of prostate specific antigen (PSA); PSA is a serine protease. The activity of PSA is much like that of the markers measured in patients with leukoplakia/erythroplakia. Elevated PSA levels were measured in blood samples taken from the patient with BPH taking BBIC. It was observed that BBIC treatment resulted in elevated levels of PSA that increased in a linear fashion with each succeeding dose of BBIC taken during the 8 day period. During the period of treatment with BBIC the patient claimed to have relief of the symptoms associated with BPH, i.e., painful urination. Upon termination of treatment with BBIC, PSA levels returned to normal but high baseline level known to be associated with BPH.

What is claimed is:

1. A composition for the treatment of cancer comprising a BBI concentrate product having at least 25 C.I. units of activity.

2. The composition of claim 1 further comprising a pharmaceutically acceptable carrier.

3. A method for treating pre-malignant tissues in an animal comprising administering a BBI concentrate product having at least 25 C.I. units of activity to an animal having pre-malignant tissue.

4. The method of claim 3 wherein the BBI Concentrate product is administered in combination with a pharmaceutically acceptable carrier.

5. The method of claim 3, wherein the pre-malignant tissue comprises breast, colon, oral mucosa, esophageal, liver, lung, hematopoietic or prostate tissue.

6. A method for preventing or inhibiting cancer in an animal comprising administering to an animal a BBI concentrate product having at least 25 C.I. units of activity.

7. The method of claim 6 wherein the BBI Concentrate product is administered in combination with a pharmaceutically acceptable carrier.

8. The method of claim 7 wherein the cancer being inhibited is breast, colon, oral mucosa, esophageal, liver, lung, hematopoietic or prostate cancer.

* * * * *